United States Patent
Xu et al.

(10) Patent No.: US 12,385,839 B2
(45) Date of Patent: Aug. 12, 2025

(54) USE OF PROTEIN IN PREDICTING DRUG PROPERTIES

(71) Applicant: HEILONGJIANG UNIVERSITY, Harbin (CN)

(72) Inventors: Hongliang Xu, Harbin (CN); Qin Zhou, Harbin (CN); Li Li, Harbin (CN); Zishi Wang, Harbin (CN); Xiangshuai Li, Harbin (CN); Yue Xing, Harbin (CN); Jinsheng Gao, Harbin (CN)

(73) Assignee: HEILONGJIANG UNIVERSITY, Harbin (CN)

( * ) Notice: Subject to any disclaimer, the term of this patent is extended or adjusted under 35 U.S.C. 154(b) by 0 days.

(21) Appl. No.: 17/543,698

(22) Filed: Dec. 6, 2021

(65) Prior Publication Data

US 2022/0260495 A1    Aug. 18, 2022

(30) Foreign Application Priority Data

Feb. 9, 2021    (CN) .......................... 202110178985.7

(51) Int. Cl.
*G01N 21/64* (2006.01)
*G01N 21/33* (2006.01)

(52) U.S. Cl.
CPC ......... *G01N 21/6486* (2013.01); *G01N 21/33* (2013.01); *G01N 21/6428* (2013.01); *G01N 21/6456* (2013.01); *G01N 2021/6432* (2013.01)

(58) Field of Classification Search
None
See application file for complete search history.

(56) References Cited

FOREIGN PATENT DOCUMENTS

WO    WO-0157495 A2 *   8/2001   ............. G01N 21/25

OTHER PUBLICATIONS

Celeste Morin, Hitachi F-2500 Fluorescence Spectrophotometer, Bowdoin College, 2017 (Year: 2017).*
Shimadzu, RF-5301PC, Shimadzu, 2008 (Year: 2008).*
Shimadzu, UV-2450 UV-2550, Shimadzu, 2013 (Year: 2013).*
Xu et al., Characterization of the Interaction between Eupatorin and Bovine Serum Albumin by Spectroscopic and Molecular Modeling Methods, Int. J. Mol. Sci. 2013, 14, 14185-14203 (Year: 2013).*

(Continued)

*Primary Examiner* — Maris R Kessel
*Assistant Examiner* — Mickey Huang
(74) *Attorney, Agent, or Firm* — Tutunjian & Bitetto, P.C.

(57) ABSTRACT

The present disclosure belongs to the field of application of protein, and relates to use of a protein in predicting properties of a drug. The drug comprises pesticides, human drugs and veterinary drugs, and the protein is applied in the following steps: preparing a 0.02 M phosphate buffer solution with pH value of 7.4; dissolving and diluting a protein solution with the prepared buffer solution according to a signal value to obtain a protein diluent; mixing the prepared protein diluent with the drug to be tested in a molar ratio of 1: (1-300) to obtain a mixed solution to be tested, and predicting the drug properties by using fluorescence spectrum, synchronous fluorescence, three-dimensional fluorescence, circular dichroism spectrum, UV-Vis absorption spectrum, linear spectrum or band spectrum.

3 Claims, 14 Drawing Sheets

(56) References Cited

OTHER PUBLICATIONS

Liu et al., The Bio-Safety Concerns of Three Domestic Temporary Hair Dye Molecules: Fuchsin Basic, Victoria Blue B and Basic Red 2, Molecules 2019, 24, 1744 (Year: 2019).*
Chen et al., Binding of triclosan to human serum albumin: insight into the molecular toxicity of emerging contaminant, Environ Sci Pollut Res (2012) 19:2528-2536 (Year: 2012).*

* cited by examiner

USE OF PROTEIN IN PREDICTING DRUG PROPERTIES

CROSS REFERENCE TO RELATED APPLICATION

This patent application claims the benefit and priority of Chinese Patent Application No. 202110178985.7, entitled "USE OF PROTEIN IN PREDICTING DRUG PROPERTIES" filed with the China National Intellectual Property Administration on Feb. 9, 2021, the disclosure of which is incorporated by reference herein in its entirety as part of the present application.

TECHNICAL FIELD

The disclosure belongs to the field of protein application, and particularly relates to the use of a protein in predicting drug properties.

BACKGROUND ART

All new drugs must undergo a series of tests before entering the market. Toxicity is an important index, and is the main reason for the failure of drug development. It is reported that toxicity will cause about 30% of candidate drugs to be discarded. In particular, many drugs have to be withdrawn from the market due to the high toxicity in the later stage of research and development, which causes a waste of both time and cost. A few years ago, it was suggested that toxicological assessment should be started at the early stage of drug discovery process of small molecules. Early evaluation of the drug toxicity is helpful to achieve accurate drug design and synthesis, thus effectively shortening the drug development cycle and reducing the cost.

Many strategies and new methods for early prediction of drug toxicity have been put forward to screen out the most promising candidate drugs. Among the others, it is worth noting that the SAR research, cytotoxicity determination and biomarker detection are of great significance. However, all the detecting methods have shortcomings, for example, "SAR" research is straightforward and highly sensitive, but it is not specific, and thus false positive results may lead to the consumption of new promising candidate drugs. Cytotoxicity test is usually one of the earliest toxicity tests. However, this method requires more stringent experimental conditions and a more extended period. In addition, due to lack of metabolism, cell type sensitivity, and different culture conditions, the ability of in vitro cytotoxicity test to predict the toxicity of target organs in vivo are often questioned.

Biomarker detection is a crucial tool to discover and develop biomarkers. However, its development involves some challenges. For example, the scientific reasons underlying some biomarkers cannot always be verified, which brings challenges to the verification and identification of biomarkers. In addition, the development of biomarkers may be related to other testing requirements, which may increase the development cost. In view of the importance of early toxicity assessment, this application aims to find a new method for predicting drug toxicity more easily, quickly and universally.

Pesticides play an extremely important role in maintaining food security and reducing harvest losses. However, most pesticides are toxic and pose a threat to the environment, human beings, animals and other organisms. With the enhancement of human awareness of environmental protection, many products having good activity but strong toxicity are banned in pesticides. Particularly, carbamate pesticides are widely used in agricultural production, but once they enter human body, they may cause acute or chronic poisoning. The reason why carbamate pesticides are toxic to the human body is that they can inhibit the activity of cholinesterase, so it is necessary to predict the toxicity of drugs to the human body.

SUMMARY

In order to overcome the deficiencies of the prior art, the present disclosure provides the use of a protein in predicting drug properties, and studies the toxicity prediction of carbamate pesticides through binding information of the protein and carrier protein, and the relationship of the protein and toxicity.

The use of a protein of the present disclosure in predicting drug properties is provided, wherein the protein is used for predicting drug properties, and the drugs comprise pesticides, human drugs and veterinary drugs.

In some embodiments, the protein comprises carrier proteins such as human serum albumin (HSA), and bovine serum albumin (BSA), and proteins such as hemoglobin, globulin, myogenic, collagen, zymoprotein, bee protein and fish protein.

In some embodiments, the protein is applied in the following steps:

(1) preparing a buffer solution, comprising: preparing a 0.02 M phosphate buffer solution with pH value of 7.4;

(2) preparing a protein diluent, comprising: dissolving and diluting a protein solution with the buffer solution prepared in step (1) according to a signal value to obtain a protein diluent;

(3) preparing a detection solution, comprising: mixing the protein diluent prepared in step (2) with a drug to be tested in a molar ratio of 1: (1-300) to obtain a mixed solution to be tested, and predicting the drug properties by using fluorescence spectrum, synchronous fluorescence, three-dimensional fluorescence, circular dichroism spectrum, UV-Vis absorption spectrum, linear spectrum, or band spectrum.

In some embodiments, the molar ratio of the protein diluent to the drug to be tested is 1: (1-300).

In some embodiments, the drug toxicity is predicted by using fluorescence emission spectrum, comprising:

preheating the mixed solution to be tested at 283-232 K for 3 minutes, and measuring the emission spectra of human serum albumin (HSA) with different drugs at 300-500 nm , the excitation wavelength is set at 280 nm , and the slit width for both excitation and emission are 15 nm ; the HSA concentration is kept constant at $5\times10^{-7}$ M, and the pesticide concentration is $(0-105)\times10^{-7}$ M;

the internal filtering effect of fluorescence signal is corrected according to the following formula:

$$F_{cor}=F_{obs}\exp[(A_{ex}+A_{em})/2]$$

in this formula, $F_{cor}$ and $F_{obs}$ represent corrected fluorescence signal and observed fluorescence signal, respectively, and $A_{ex}$ and $A_{em}$ represent absorbance of the mixed solution to be tested at excitation wavelength and emission wavelength, respectively.

The quenching constant, binding constant, number of binding sites, binding distance and free energy of different drugs are obtained by the fluorescence emission spectra, and then a model is constructed using a BP neural network. In the prediction process, $LD_{50}$ value of the pesticide is obtained by inputting the above five values, detected by fluorescence spectrum, of the pesticide to be tested into the model, and the toxicity grade can be obtained according to the criteria for pesticide hazard classification from the World Health Organization, thus completing the toxicity prediction.

In some embodiments, the use of the present application further comprises a step of measuring the influence of the drug on conformational changes of human serum albumin by synchronous fluorescence spectrum, specifically comprising:

preheating the mixed solution to be tested at 283-232 K for 2-5 minutes, and setting the scanning speed at 300 nm/min, scanning the excitation spectra and emission spectra simultaneously in a range of 200-400 nm to obtain synchronous fluorescence spectra of HSA with different drugs, and interval between excitation wavelength and emission wavelength is set at 15 nm and 60 nm, respectively; when $\Delta\lambda=15$ nm, the HSA concentration is kept at $2\times10^{-6}$ M, and the pesticide concentration is $(0-42)\times10^{-6}$ M, when $\Delta\lambda=60$ nm, the HSA concentration is maintained at $5\times10^{-7}$ M, and the pesticide concentration is $(0-105)\times10^{-7}$ M.

In some embodiments, the influence of the drug on conformational change of human serum albumin is measured by three-dimensional fluorescence spectrum, specifically comprising:

preheating the mixed solution to be tested at 283-232 K for 2-5 minutes, and setting the scanning speed at 300 nm/min, the samples of $8\times10^{-8}$ M HSA, and of $8\times10^{-8}$ M HSA mixed with $8\times10^{-7}$ M pesticide are analyzed by a three-dimensional fluorescence spectrum, the emission wavelength is recorded as 250-500 nm, the initial excitation wavelength is set at 210 nm, the excitation interval is 10 nm, and the slit width for both excitation and emission are 15 nm.

In some embodiments, the changes of secondary structure of human serum albumin is measured by circular dichroism spectrum, specifically comprising:

preheating the mixed solution to be tested at 283-232 K for 2-5 minutes, and a CD spectrum of HSA is recorded in a wavelength range of 200-500 nm, the HSA concentration is kept at $2\times10^{-6}$ M, and the pesticide concentration is $(0-20)\times10^{-6}$ M.

In some embodiments, the influence of the drug on HSA is measured by a UV-Vis absorption spectrum, specifically comprising:

preheating the mixed solution to be tested at 283-232 K for 2-5 minutes, recording the UV-Vis spectrum of HSA with various drugs in a range of 190-500 nm, the wavelength interval is set at 0.5 nm and the slit width is set at 2 nm; the HSA concentration is kept at $5\times10^{-6}$ M, and is titrated with $(0-175)\times10^{-6}$ M of pesticide.

M in the above represents the unit of mol/L.

According to the use of the protein of the disclosure in predicting the drug properties, the interaction information between the drug and the protein is studied through an UV-Vis spectrum, fluorescence, synchronous fluorescence, three-dimensional fluorescence and circular dichroism (CD) spectrum system. In order to predict the toxicity more easily with the least equipment and time, a BP neural network model among five indexes (quenching constant, number of binding sites, binding constant, free energy, binding distance) is obtained through fluorescence spectrum and toxicity and are used to predict drug properties, which has important practical significance for the development of drug research and development industry.

DETAILED DESCRIPTION OF THE EMBODIMENTS

Figure 1:
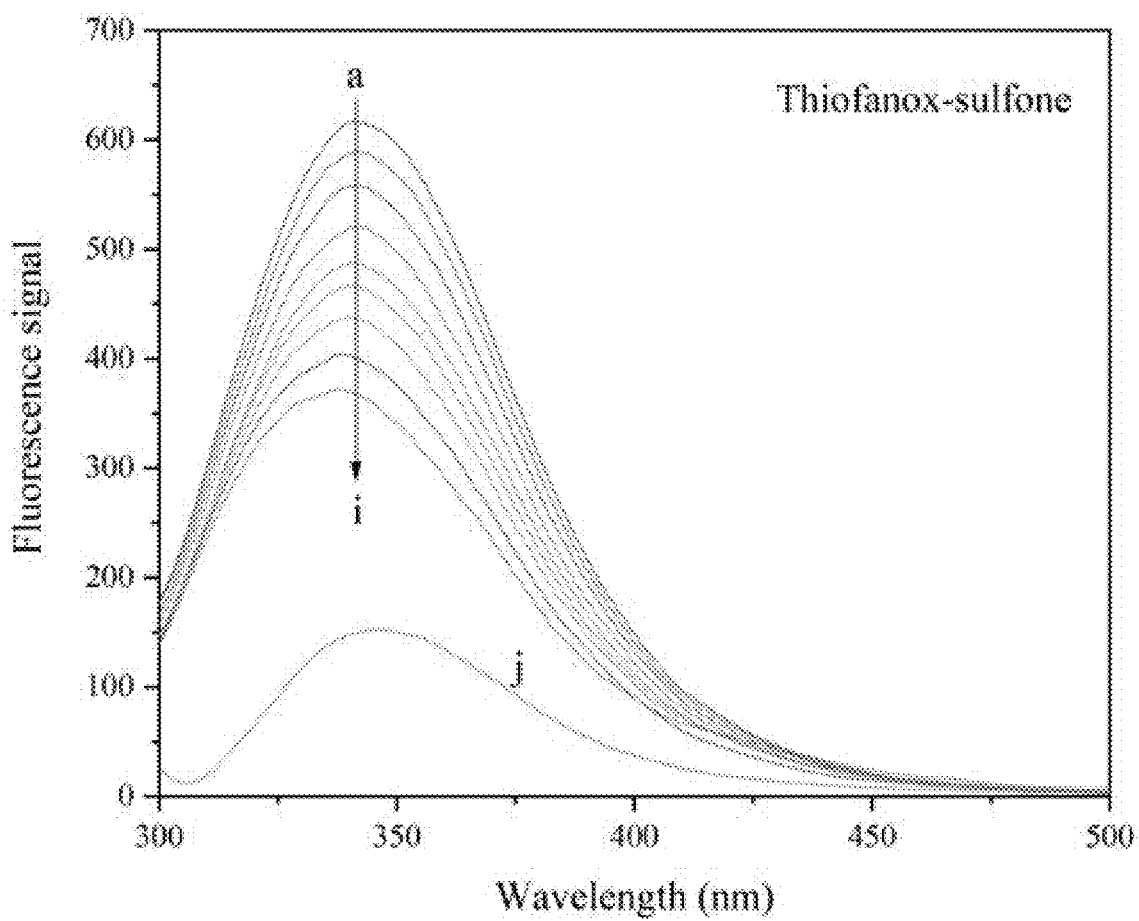
FIG. 1 is the fluorescence emission spectrum of HSA in the presence of thiofanox sulfone with different concentrations, in which (a) represents $5\times10^{-7}$ M HSA; (b-i) represents $5\times10^{-7}$ M HSA in the presence of 5, 15, 30, 45, 60, 75, 90 and $105\times10^{-7}$ M thiofanox sulfone; (j) represents $105\times10^{-7}$ M thiofanox sulfone only; pH=7.4, T=310 K.

The present disclosure provides the use of a protein in predicting drug properties, in which the drugs include pesticides, human drugs and veterinary drugs.

The pesticides include carbamate pesticides, specifically including aldicarb, thiofanox sulfone, oxamyl, thiofanox sulfone, carbofuran, thiofanox, methomyl, aldicarb sulfone, aminocarb, promecarb, propoxur, dimethacarb, ethiofencarb, XMC (3,5-xylyl methylcarbamate), metolcarb, fenobucarb, isoprocarb and butoxycarboxim.

The human drugs include penicillins, cephalosporins, aminoglycosides, macrolides, tetracyclines, chloramphenicols and lincosamides, amino acids, polypeptides, proteins, enzymes, nucleic acids, polysaccharides, lipids, biogenic amines and the like.

The veterinary drugs include penicillin sodium, ampicillin, amoxicillin, ceftiofur, erythromycin, tylosin, tilmicosin, tetracycline, doxycycline, oxytetracycline, spectinomycin, gentamicin, kanamycin, thiamphenicol, florfenicol, enrofloxacin, ciprofloxacin, danofloxacin, sulfadiazine, mequidox, sarafloxacin hydrochloride, avermectin, metronidazole, salinomycin and the like.

The protein include carrier proteins such as human serum albumin (HSA) and bovine serum albumin, as well as hemoglobin, globulin, myogenic, collagen, zymoprotein, bee protein and fish protein.

The use of the protein of the present disclosure in predicting drug properties, including:

(1) preparation of buffer solution: a 0.02 M phosphate buffer solution with pH value of 7.4 was prepared;

(2) preparation of protein diluent: a protein solution was dissolved and diluted with the buffer solution prepared in step (1) according to a signal value to obtain a protein diluent (the maximum signal value of the instrument is set at 1000, if the signal value is higher than 1000, decreasing the concentration of the protein solution, if the signal value is lower than 1000, increasing the concentration of the protein solution; in principle, the signal value is controlled lower than 1000, and in this case, the higher the concentration, the better);

(3) preparation of detection solution: the protein diluent prepared in step (2) was mixed with the drug to be tested in a molar ratio of 1: (1-300) to obtain a mixed solution to be tested, and a drug properties were predicted by using fluorescence spectrum, synchronous fluorescence, three-dimensional fluorescence, circular dichroism spectrum, linear spectrum, or band spectrum.

Hereafter, carbamate pesticides and HSA were used as examples to illustrate the influence of carbamate pesticides on HSA:

(1) Selection of finished pesticide;

fifteen kinds of carbamate pesticides were selected, including thiofanox sulfone, oxamyl, thiofanox sulfone, carbofuran, thiofanox, methomyl, aminocarb, promecarb, propoxur, dimethacarb, ethiofencarb, XMC (3,5-xylyl methylcarbamate), metolcarb, isoprocarb and butoxycarboxim.

(2) Preparation of PBS solution.

a. 0.2 M PBS solution 10.5471 g of NaCl, 0.2637 g of KCl, 1.8985 g of $Na_2HPO_4$ and 0.3164g of $KH_2PO_4$ were weighed separately and mixed, 800 ml of double-distilled water was added, the pH was adjusted to 7.4 with NaOH solution, and the resulting solution was made up to 1000 ml.

Note: NaOH solution had a concentration of 1 M, which included 1.2 g of solid NaOH and 30 ml water;

b. 0.02 M PBS solution (for use in dilution of protein).
10 ml of 0.2 M PBS was taken and made up to 100 ml;
15 ml of 0.2 M PBS was taken and made up to 150 ml.
The diluted solutions were filtered and placed in a refrigerator at 4° C. for later use.

c. Instruments and supplies required for this step:
500 ml conical flask, 1000 ml/500 ml beaker, glass rod, 50 ml beaker, pH meter, pH meter calibration solution, wash bottle, waste tank, filter paper, 1 ml pipette, pipette tip, needle tube, filter cap, analytical balance, weighing paper, 150 ml/200 ml beaker*2, disposable dropper.

(3) Preparation of HSA solution.

a. $10^{-4}$ M HSA mother liquor.

0.0067 g of HSA was weighed and 1 ml of 0.2 M PBS was added;
0.0033 g of HSA was weighed and 0.5 ml of 0.2 M PBS was added.

b. HSA solution for experiment.

The HSA solution was gradually diluted, and the final HSA solution concentration was determined according to the signal value;

$4 \times 10^{-7}$ M HSA was used for fluorescence and $5 \times 10^{-6}$ M HSA was used for ultraviolet, which could be used as a reference.

c. Instruments and supplies required for this step:
1.5 ml/1 ml centrifuge tube, analytical balance, weighing paper, HSA pure product, (2.5 ul, 10 ul, 20 ul, 30ul, 50ul, 1 ml) pipette and pipette tip.

(4) Preparation of pesticide solution.

a. $10^{-2}$ M pesticide mother liquor.

The pesticide standard was weighed and diluted with ethanol.

b. Pesticide solution for experiment.

The pesticide solution was serially diluted according to the HSA concentration and the interaction ratio.

c. Instruments and supplies required for this step:
1 ml/1.5 ml/5 ml centrifuge tube, ethanol, pipette and pipette tip.

The above-mentioned prepared pesticide (taking thiofanox sulfone as an example) and HSA solution were used for detection by fluorescence spectrum, synchronous fluorescence, three-dimensional fluorescence, circular dichroism spectrum and UV-Vis absorption spectrum, respectively. The detection was conducted as follows:

1. The toxicity of carbamate pesticides was predicted by using fluorescence emission spectrum, specifically comprising:

the mixed solution to be tested was preheated at 283-232 K for 3 minutes, and the emission spectrum of HSA with carbamate pesticides was measured at 300-500 nm. The excitation wavelength was set at 280 nm, and the slit width for both excitation and emission was 15 nm; the HSA concentration was kept constant at $5 \times 10^{-7}$ M, and the pesticide concentration was $(0-105) \times 10^{-7}$ M.

The internal filtering effect of fluorescence signal was corrected according to the following formula:

$$F_{cor} = F_{obs} \exp[(A_{ex} + A_{em})/2] \quad (1);$$

in this formula, $F_{cor}$ and $F_{obs}$ represent corrected fluorescence signal and observed fluorescence signal, respectively, and $A_{ex}$ and $A_{em}$ represent absorbance of the mixed solution to be tested at excitation wavelength and emission wavelengths, respectively; the quenching constant, number of binding sites, binding constant, free energy and binding distance of different drugs were obtained by fluorescence emission spectra, and a BP neural network model was obtained. Specifically, they were obtained as follows:

(1) The influence of carbamate pesticides on fluorescence quenching of HSA

Aromatic amino acids (tryptophan residues, tyrosine residues and phenylalanine residues) were the only amino acid residues in HSA that could emit fluorescence. The intrinsic fluorescence of HSA was mainly induced by tryptophan at position 214. Taking thiofanox sulfone as an example, the fluorescence emission spectra without/with thiofanox sulfone at 310 K were shown in FIG. 1. It can be seen that the fluorescence signal of HSA decreases with the titration of pesticides, accompanied by a blue shift, indicating that the fluorescence of HSA has been quenched by thiofanox sulfone. At the same time, other 14 carbamate pesticides (oxamyl, thiofanox sulfone, carbofuran, thiofanox, methomyl, aminocarb, promecarb, propoxur, dimethacarb, ethiofencarb, XMC (3,5-xylyl methylcarbamate), metolcarb, isoprocarb and butoxycarboxim) were detected by this method, and HSA was also quenched by other 14 carbamate pesticides.

(2) Quenching mechanism of carbamate pesticides on HSA.

Generally, quenching is divided into dynamic quenching and static quenching, and their difference lies in their dependence on temperature and viscosity. Dynamic quenching mainly depends on diffusion, so the quenching constant of fluorescent complexes increases with the increase of temperature. On the contrary, the increase of temperature may lead to the decrease of stability of complexes, so the static quenching constant decreases.

There is a linear relationship between F0/F and [Q] to distinguish whether it is static quenching or dynamic quenching. The fluorescence quenching data are analyzed by Stern-Volmer equation to clarify the quenching mechanism:

$$F_0/F = 1 + K_{SV}[Q] = 1 + K_q \tau_0 [Q] \qquad (2);$$

in the formula, F0 and F are fluorescence signals with/without quencher, respectively. $K_{sv}$ is Stern-Volmer quenching constant; $K_q$ is a quenching rate constant of biomolecules; $\tau_0$ is the average lifetime of biomolecules without quencher (about $10^{-8}$ s); [Q] is the concentration of quencher.

The maximum dynamic quenching rate constant of all kinds of quenchers on polymers was $2.0 \times 10^{10}$ L·mol$^{-1}$·s$^{-1}$. Static quenching and dynamic quenching could be judged according to this value. If $K^q$ was greater than $2.0 \times 10^{10}$ L·mol$^{-1}$·s$^{-1}$, it belonged to static quenching. Otherwise, it belonged to dynamic quenching.

Figure 2:
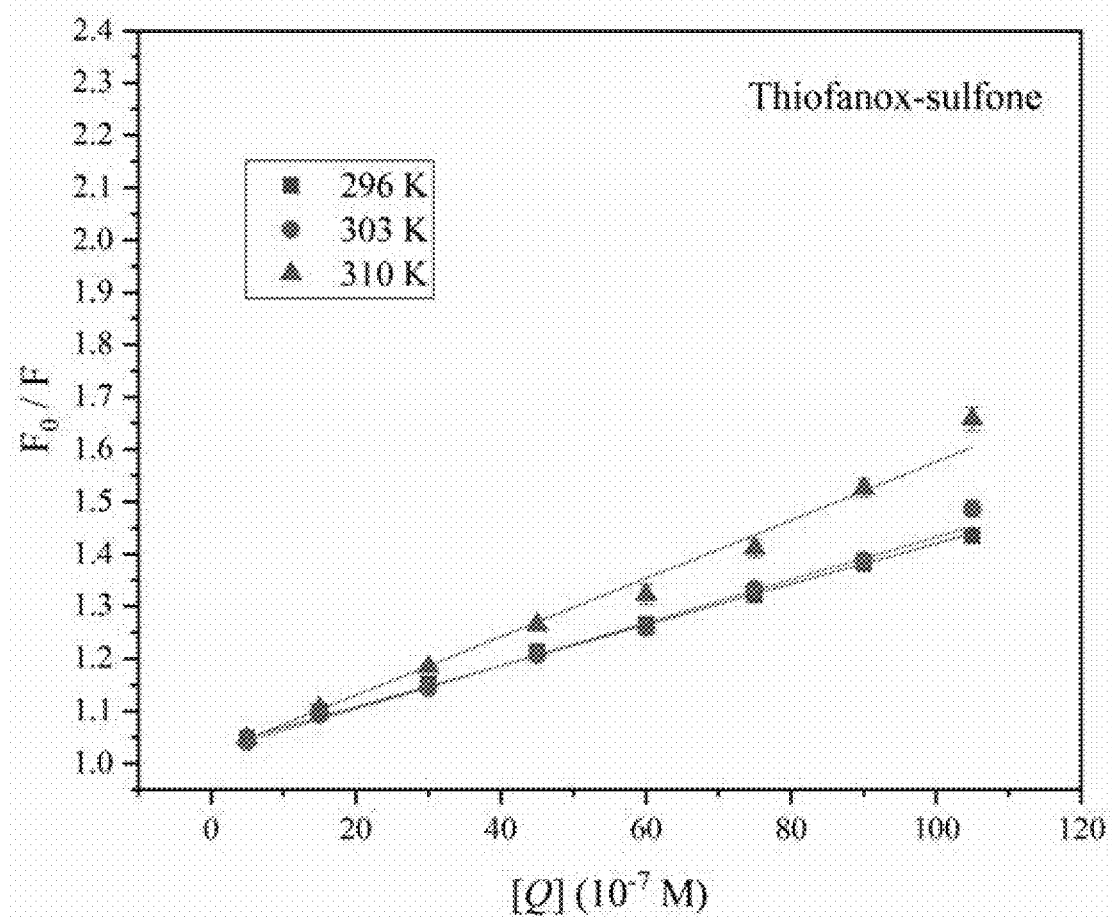
FIG. 2 is the results for Stern-Volmer quenching of the fluorescence of HSA with thiofanox sulfone at different temperatures, in which [Q] represents the concentration of quencher (thiofanox sulfone), FO represents fluorescence signal without quencher, and F represents fluorescence signal with quencher, and a pH being 7.4.

Stern-Volmer diagram of all pesticides with HSA is shown in FIG. 2, and $K_{sv}$ and $K_q$ of other drugs is calculated in Table 1. The value of $K^q$ is greater than the maximum fractional collision quenching constant ($2.0 \times 10^{10}$ L·mol$^{-1}$·s$^{-1}$). At these three temperatures, the quenching properties of biomacromolecules should be static. On the other hand, the calculated $K_{sv}$ value increased with the increase of temperature, which indicated that there was dynamic quenching of HSA by carbamate pesticides. Therefore, the interaction mechanism between carbamate pesticides and HSA was a hybrid mechanism of dynamic quenching and static quenching.

TABLE 1

Information interaction between 15 carbamate pesticides and HSA.

| Substance name | T (K) | $K_{sv}$ ($10^4$ M$^{-1}$) | $K_q$ ($10^{12}$ M$^{-1}$s$^{-1}$) | n | $K_a$ (M$^{-1}$) | $\Delta H^0$ (KJ·mol$^{-1}$) | $\Delta S^0$ (J·mol$^{-1}$·K$^{-1}$) | $\Delta G^0$ (KJ·mol$^{-1}$) | R(nm) |
|---|---|---|---|---|---|---|---|---|---|
| Thiofanox-sulfone | 296 | 3.906 ± 0.043 | 3.906 ± 0.043 | 0.719 ± 0.011 | (1.559 ± 0.162) × 10$^3$ | | | −18.004 | |
| | 303 | 4.102 ± 0.034 | 4.102 ± 0.034 | 0.786 ± 0.008 | (3.514 ± 0.247) × 10$^3$ | 98.120 | 392.314 | −20.751 | |
| | 310 | 5.574 ± 0.138 | 5.574 ± 0.138 | 0.848 ± 0.004 | (9.450 ± 0.597) × 10$^3$ | | | −23.497 | 2.907 |
| Oxamyl | 296 | 5.229 ± 0.185 | 5.229 ± 0.185 | 0.774 ± 0.016 | (3.914 ± 0.713) × 10$^3$ | | | −20.331 | |
| | 303 | 5.735 ± 0.073 | 5.735 ± 0.073 | 0.789 ± 0.004 | (5.139 ± 0.171) × 10$^3$ | 32.515 | 178.534 | −21.581 | |
| | 310 | 6.605 ± 0.058 | 6.605 ± 0.058 | 0.807 ± 0.003 | (7.112 ± 0.194) × 10$^3$ | | | −22.831 | 2.564 |
| Thiofanox-sulfoxide | 296 | 3.284 ± 0.040 | 3.284 ± 0.040 | 0.707 ± 0.009 | (1.127 ± 0.100) × 10$^3$ | 50.812 | 230.219 | −17.333 | |
| | 303 | 4.237 ± 0.067 | 4.237 ± 0.067 | 0.726 ± 0.003 | (1.906 ± 0.103) × 10$^3$ | | | −18.944 | |
| | 310 | 5.339 ± 0.093 | 5.339 ± 0.093 | 0.746 ± 0.006 | (2.861 ± 0.176) × 10$^3$ | | | −20.556 | 1.702 |
| Carbofuran | 296 | 5.563 ± 0.123 | 5.563 ± 0.123 | 0.797 ± 0.002 | (5.417 ± 0.156) × 10$^3$ | | | −21.112 | |
| | 303 | 7.239 ± 0.082 | 7.239 ± 0.082 | 0.822 ± 0.002 | (9.360 ± 0.242) × 10$^3$ | 64.326 | 288.639 | −23.132 | |
| | 310 | 8.770 ± 0.088 | 8.770 ± 0.088 | 0.862 ± 0.002 | (1.765 ± 0.031) × 10$^4$ | | | −25.153 | 1.938 |
| Thiofanox | 296 | 3.871 ± 0.035 | 3.871 ± 0.035 | 0.714 ± 0.014 | (1.454 ± 0.264) × 10$^3$ | | | −17.949 | |
| | 303 | 4.728 ± 0.064 | 4.728 ± 0.064 | 0.725 ± 0.005 | (2.016 ± 0.106) × 10$^3$ | 31.025 | 165.452 | −19.107 | |
| | 310 | 5.876 ± 0.198 | 5.876 ± 0.198 | 0.730 ± 0.003 | (2.567 ± 0.071) × 10$^3$ | | | −20.265 | 1.883 |
| Methomyl | 296 | 3.401 ± 0.068 | 3.401 ± 0.068 | 0.661 ± 0.003 | (6.830 ± 0.170) × 10$^2$ | | | −16.131 | |
| | 303 | 4.025 ± 0.136 | 4.025 ± 0.136 | 0.727 ± 0.002 | (1.727 ± 0.160) × 10$^3$ | 89.675 | 357.453 | −18.633 | |
| | 310 | 5.288 ± 0.093 | 5.288 ± 0.093 | 0.766 ± 0.002 | (3.536 ± 0.105) × 10$^3$ | | | −21.135 | 2.145 |
| Aminocarb | 296 | 3.151 ± 0.089 | 3.151 ± 0.089 | 0.649 ± 0.005 | (5.678 ± 0.451) × 10$^2$ | | | −15.553 | |
| | 303 | 3.409 ± 0.059 | 3.409 ± 0.059 | 0.669 ± 0.006 | (8.021 ± 0.741) × 10$^2$ | 43.878 | 200.780 | −16.958 | |
| | 310 | 3.905 ± 0.179 | 3.905 ± 0.179 | 0.699 ± 0.003 | (1.272 ± 0.024) × 10$^3$ | | | −18.364 | 2.215 |
| Promecarb | 296 | 2.409 ± 0.154 | 2.409 ± 0.154 | 0.645 ± 0.004 | (4.109 ± 0.141) × 10$^2$ | | | −14.733 | |
| | 303 | 3.705 ± 0.060 | 3.705 ± 0.060 | 0.704 ± 0.008 | (1.216 ± 0.014) × 10$^3$ | 125.885 | 475.061 | −18.058 | |
| | 310 | 5.817 ± 0.219 | 5.817 ± 0.219 | 0.769 ± 0.009 | (4.146 ± 0.049) × 10$^3$ | | | −21.383 | 2.316 |
| Propoxur | 296 | 3.425 ± 0.132 | 3.425 ± 0.132 | 0.706 ± 0.014 | (1.260 ± 0.209) × 10$^3$ | | | −17.536 | |
| | 303 | 4.353 ± 0.121 | 4.353 ± 0.121 | 0.729 ± 0.013 | (1.898 ± 0.304) × 10$^3$ | 47.825 | 220.816 | −19.082 | |
| | 310 | 5.053 ± 0.120 | 5.053 ± 0.120 | 0.757 ± 0.011 | (3.032 ± 0.341) × 10$^3$ | | | −20.627 | 3.138 |
| Trimethacarb | 296 | 3.043 ± 0.160 | 3.043 ± 0.160 | 0.694 ± 0.002 | (9.546 ± 0.118) × 10$^2$ | | | −16.857 | |
| | 303 | 4.204 ± 0.100 | 4.204 ± 0.100 | 0.696 ± 0.003 | (1.268 ± 0.092) × 10$^3$ | 33.988 | 171.775 | −18.059 | |
| | 310 | 4.778 ± 0.093 | 4.778 ± 0.093 | 0.713 ± 0.005 | (1.782 ± 0.036) × 10$^3$ | | | −19.262 | 2.954 |
| Ethiofencarb | 296 | 2.562 ± 0.137 | 2.562 ± 0.137 | 0.613 ± 0.003 | (3.428 ± 0.066) × 10$^2$ | | | −14.374 | |
| | 303 | 3.301 ± 0.074 | 3.301 ± 0.074 | 0.645 ± 0.009 | (5.863 ± 0.559) × 10$^2$ | 55.921 | 237.483 | −16.037 | |
| | 310 | 4.135 ± 0.166 | 4.135 ± 0.166 | 0.674 ± 0.002 | (9.563 ± 0.218) × 10$^2$ | | | −17.699 | 2.363 |
| XMC | 296 | 4.145 ± 0.187 | 4.145 ± 0.187 | 0.734 ± 0.005 | (1.854 ± 0.120) × 10$^3$ | | | −18.450 | |
| | 303 | 4.362 ± 0.151 | 4.362 ± 0.151 | 0.779 ± 0.012 | (3.404 ± 0.472) × 10$^3$ | 73.779 | 311.582 | −20.631 | |
| | 310 | 4.830 ± 0.108 | 4.830 ± 0.108 | 0.832 ± 0.006 | (7.187 ± 0.498) × 10$^3$ | | | −22.812 | 2.033 |
| Metolcarb | 296 | 3.261 ± 0.020 | 3.261 ± 0.020 | 0.564 ± 0.012 | (2.249 ± 0.362) × 10$^2$ | | | −13.291 | |
| | 303 | 3.415 ± 0.159 | 3.415 ± 0.159 | 0.587 ± 0.001 | (3.394 ± 0.050) × 10$^2$ | 48.673 | 209.338 | −14.756 | |
| | 310 | 4.442 ± 0.118 | 4.442 ± 0.118 | 0.616 ± 0.003 | (5.497 ± 0.211) × 10$^2$ | | | −16.222 | 2.525 |

TABLE 1-continued

Information interaction between 15 carbamate pesticides and HSA.

| Substance name | T (K) | $K_{sv}$ ($10^4$ M$^{-1}$) | $K_q$ ($10^{12}$ M$^{-1}$s$^{-1}$) | n | $K_a$ (M$^{-1}$) | ΔH° (KJ·mol$^{-1}$) | ΔS° (J·mol$^{-1}$·K$^{-1}$) | ΔG° (KJ·mol$^{-1}$) | R(nm) |
|---|---|---|---|---|---|---|---|---|---|
| Isoprocarb | 296 | 2.175 ± 0.070 | 2.175 ± 0.070 | 0.669 ± 0.004 | (4.875 ± 0.284) × $10^2$ | | | −15.260 | |
| | 303 | 2.758 ± 0.048 | 2.758 ± 0.048 | 0.689 ± 0.004 | (7.701 ± 0.377) × $10^2$ | 44.910 | 203.281 | −16.683 | |
| | 310 | 3.015 ± 0.043 | 3.015 ± 0.043 | 0.712 ± 0.009 | (1.111 ± 0.122) × $10^3$ | | | −18.106 | 2.338 |
| Butoxy-carboxim | 296 | 2.888 ± 0.064 | 2.888 ± 0.064 | 0.658 ± 0.002 | (5.827 ± 0.213) × $10^2$ | | | −15.634 | |
| | 303 | 4.798 ± 0.112 | 4.798 ± 0.112 | 0.679 ± 0.002 | (1.202 ± 0.037) × $10^3$ | 81.824 | 329.251 | −17.939 | |
| | 310 | 6.264 ± 0.074 | 6.264 ± 0.074 | 0.725 ± 0.001 | (2.617 ± 0.076) × $10^3$ | | | −20.244 | 1.964 |

(3) Determination of binding sites and binding constants between carbamate pesticides and HSA.

In this part, the binding sites and binding constants between carbamate pesticides and HSA were calculated. The following formula was used to calculate the number of binding sites (n) and the binding constant (Ka) of carbamate pesticides and HSA:

$$\log[(F_0-F)/F] = \log K_a + n\log[Q] \quad (3);$$

in the formula, $F_0$ is the relative fluorescence signal of HSA, F is the relative fluorescence signal of HSA and thiofanox sulfone, $K_a$ is the binding constant, n is the number of binding sites, and [Q] is the concentration of thiofanox sulfone.

Figure 3:
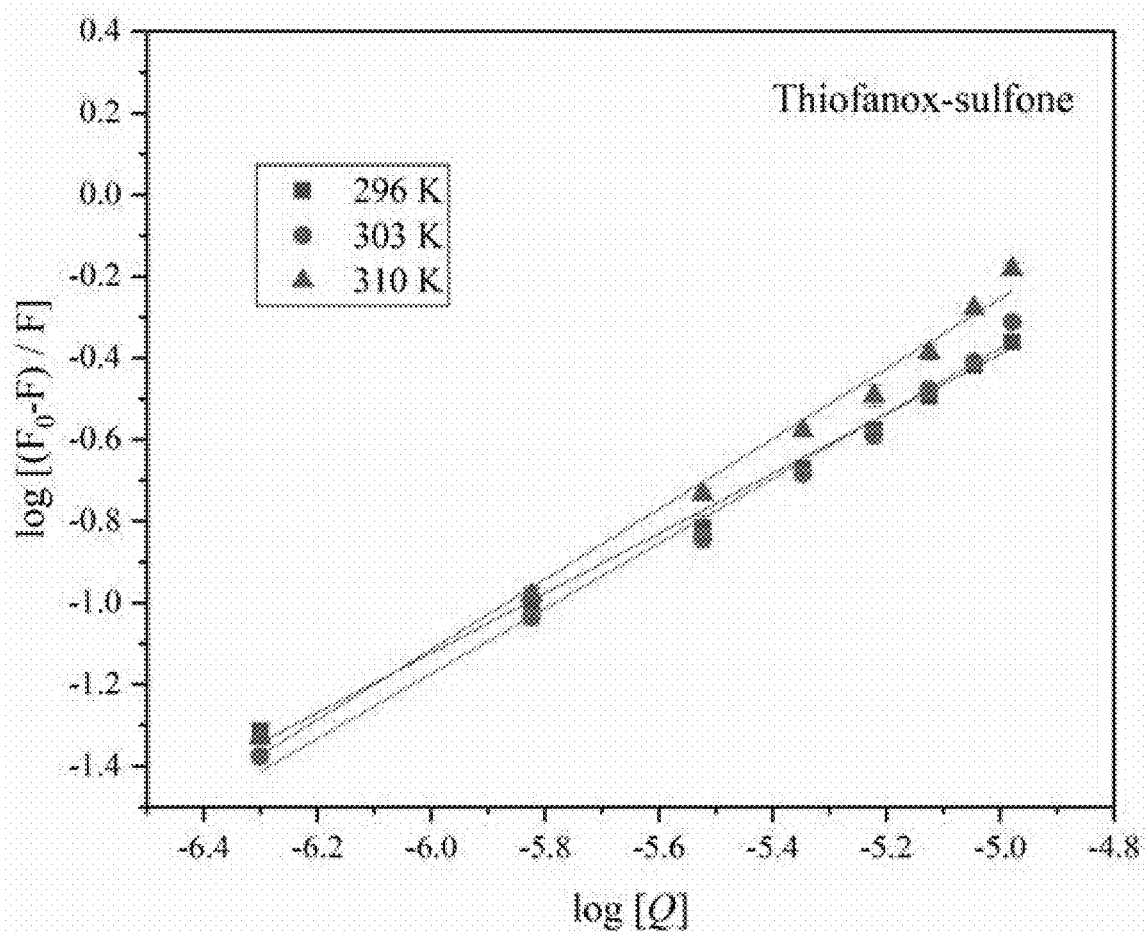
FIG. 3 shows the relationship between logarithm $[(F_0-F)/F]$ and logarithm [Q] of the interaction between thioxasulfone and HSA at different temperatures, in which [Q] represents the concentration of quencher (thiofanox sulfone); F0 represents fluorescence signal without quencher; F represents fluorescence signal with quencher, and a pH being 7.4.

The intercept and slope of the log $[(F_0-F)/F]$-log [Q] curve are obtained from FIG. 3 and Formula (3), and the number of binding sites and binding constants at different temperatures are obtained. The number of binding sites is about 1. Table 1 lists the binding constants of carbamate pesticides and HSA.

(4) Thermodynamic parameters and binding force.

The interactions between biological molecules and drug molecules were weak intermolecular interactions, including hydrogen bonds, van der Waals forces, electrostatic forces and hydrophobic interactions. By using Van't Hoff equation, the thermodynamic constants of drug-protein interaction were obtained, and the main types of drug-protein interaction were judged according to the changes of binding constants under different conditions.

$$LnK = -\Delta H^0/RT + \Delta S^0/R \quad (4)$$

$$\Delta G^0 = \Delta H^0 - T\Delta S^0 \quad (5);$$

The constant K was similar to the binding constant at the corresponding temperature.

Figure 4:
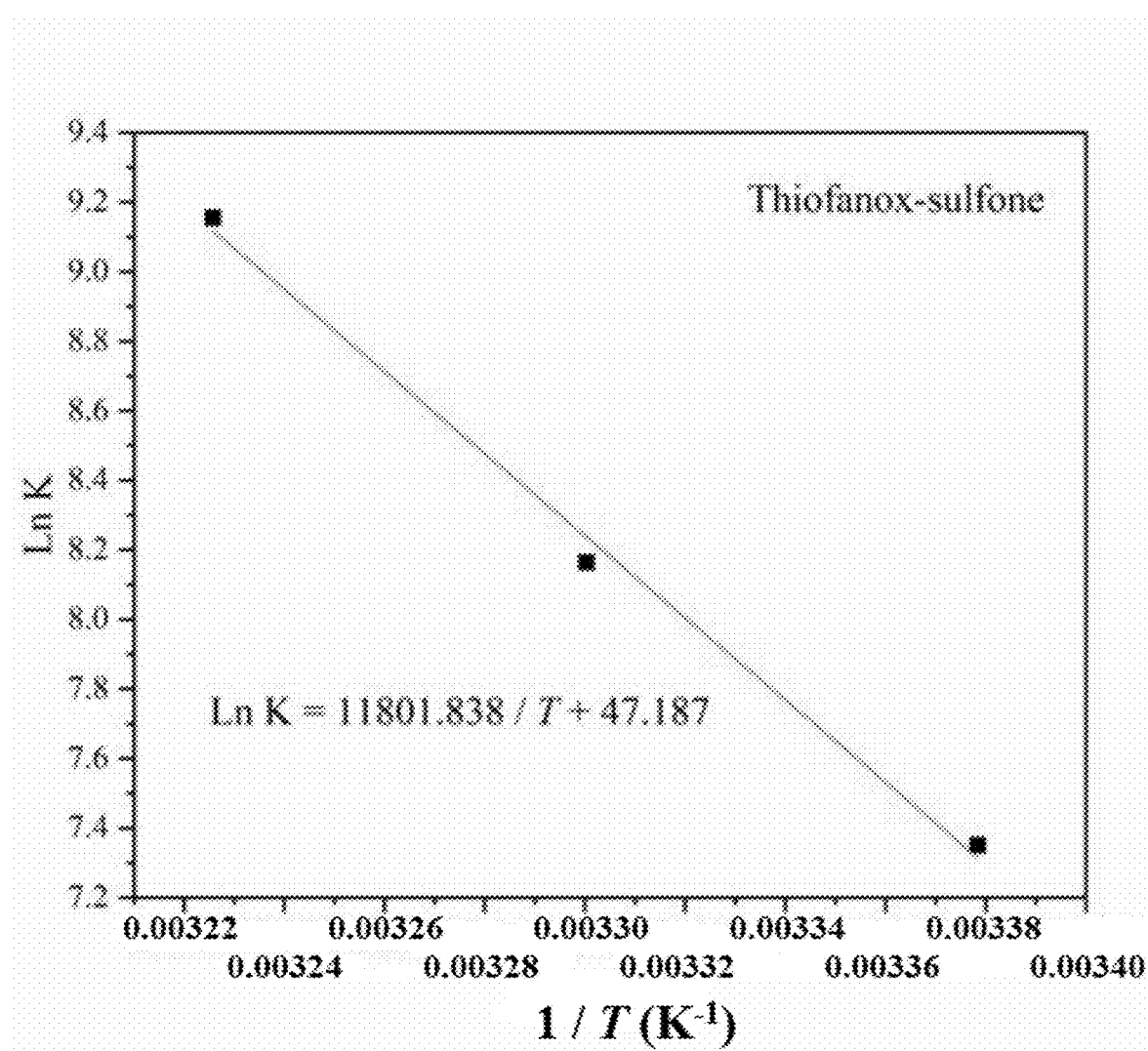
FIG. 4 shows the relationship between LnK and 1/T according to Van't Hoff equation, in which K represents binding constant, T represents absolute temperature, and pH=7.4.

FIG. 4 shows the relationship between Ln K and 1/T according to Van't Hoff equation. ΔG°, ΔH° and ΔS° can be obtained from slope and intercept, respectively. It can be seen from Table 1 that the ΔG° of interaction between all carbamate pesticides and HSA is negative, while ΔH° and ΔS° are positive. According to the thermodynamic rules for judging the binding force between macromolecules and micromolecules, when ΔH°>0 and ΔS°>0, it is a typical hydrophobic force, which can be judged that the interaction between carbamate pesticides and HSA is spontaneous, mainly through the typical hydrophobic interaction.

(5) Non-radioactive energy transfer and binding distance.

The Förster energy transfer theory was used to explain the nonradiative energy transfer between carbamate pesticides and HSA, and the binding distance between carbamate pesticides and amino acid residues was determined.

There is a relationship among energy transfer efficiency E, distance r between energy donor and energy receptor and energy transfer distance $R_0$.

$$E = 1 - F/F_0 = R_0^6/(R_0^6 + r^6) \quad (6);$$

E represents the transfer efficiency between donor and receptor, r is the average distance between donor and receptor, and $R_0$ is the critical distance when the transfer efficiency is 50%.

$$R_0^6 = 8.79 \times 10^{-}K^2N^{-4}\varphi J \quad (7)$$

$K^2$ is the orientation related to the geometry of donor and receptor of dipole. For random orientation in fluid, $K^2=2/3$; N is the average refractive index of the medium in the wavelength range with obvious spectral overlap, and the refractive index of water and organic matter is 1.336; φ is the quantum yield of donor, and the quantum yield of tryptophan in HSA is about 0.118; J represents the influence of spectral overlap between the emission spectrum of the donor and the absorption spectrum of the receptor, and can be calculated by the following formula:

$$j = \Sigma F(\lambda)\epsilon(\lambda)\lambda^4 \Delta\lambda / \Sigma F(\lambda) \Delta\lambda \quad (8);$$

F(λ) is the corrected fluorescence signal of the donor in the wavelength range from λ to (λ+Δλ), while ε(λ) is the extinction coefficient of the receptor at λ.

Figure 5:
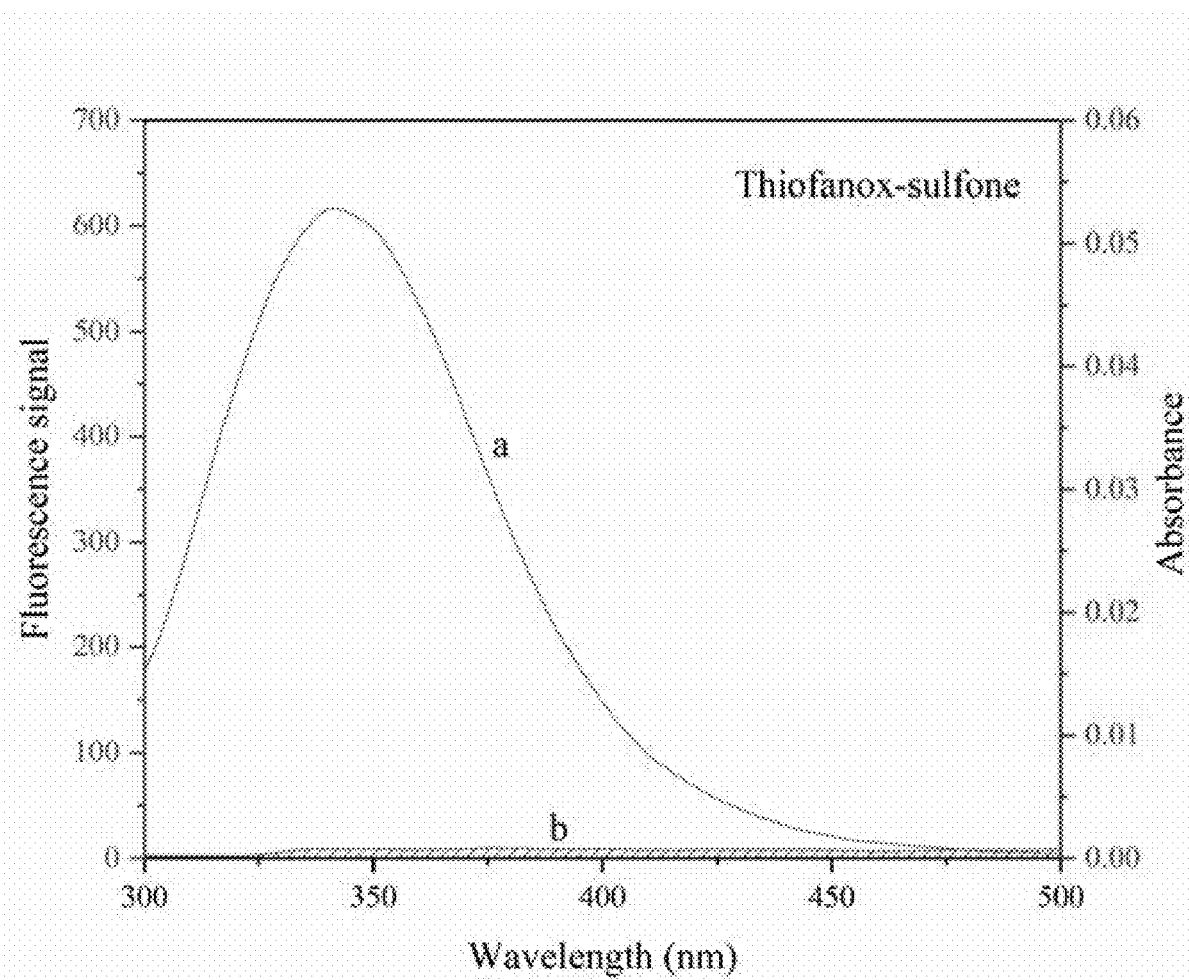
FIG. 5 shows that the fluorescence spectrum of HSA overlaps with the absorption spectrum of thiofanox sulfone, in which (a) represents $5\times10^{-7}$ M HSA, (b) represents $5\times10^{-7}$ M thiofanox sulfone, and pH=7.4, T=310 K.

The fluorescence spectrum of HSA overlapped with the absorption spectrum of carbamate pesticide, as shown in FIG. 5, and the binding distance was recorded in Table 1. The results showed that the non-radioactive energy transfer occurred between carbamate pesticide and HSA because r<8, which was consistent with the occurrence of static quenching mechanism.

The $K_{sv}$ (quenching constant), $K_a$ (binding constant), n (number of binding sites), r (binding distance) and ΔG (free energy) of different pesticides measured by the above stens are as follows:

| Toxicity | Name | $LD_{50}$ | $K_{sv}$ (37°) | Number of binding sites/n | $K_a$ (37°) | ΔG(37°) | Binding distance/r |
|---|---|---|---|---|---|---|---|
| Highly toxic 5 | aldicarb | 0.5 | 72295.50723 | 0.85079 | 12943.17386 | −24.41877 | 2.62266 |
| | thiofanox sulfone | 1.9 | 55736.87796 | 0.84760 | 9450.39640 | −23.49672 | 2.90699 |
| | oxamyl | 2.5 | 66054.55780 | 0.80743 | 7112.03116 | −22.83066 | 2.56369 |

| Toxicity | Name | $LD_{50}$ | $K_{sv}$ (37°) | Number of binding sites/n | $K_a$ (37°) | $\Delta G(37°)$ | Binding distance/r |
|---|---|---|---|---|---|---|---|
| | thiofanox sulfone | 3.8 | 53392.17364 | 0.74562 | 2860.88330 | −20.55565 | 1.70234 |
| | carbofuran | 5 | 87696.31575 | 0.86159 | 17653.90851 | −25.15253 | 1.93814 |
| Highly toxic 6 | thiofanox | 8.5 | 58762.03726 | 0.72993 | 2567.30878 | −20.26540 | 1.88336 |
| | methomyl | 14.7 | 52883.69408 | 0.76569 | 3536.34545 | −21.13504 | 2.14529 |
| | aldicarb sulfone | 20 | 39842.68547 | 0.65439 | 829.48368 | −17.29355 | 2.37645 |
| | aminocarb | 30 | 39050.24214 | 0.69851 | 1271.48503 | −18.36386 | 2.21510 |
| | promecarb | 35 | 58172.07681 | 0.76879 | 4146.31839 | −21.38347 | 2.31593 |
| | propoxur | 41 | 50525.98687 | 0.75654 | 3031.57094 | −20.62740 | 3.13760 |
| Moderately toxic 7 | dimethacarb | 178 | 47778.50539 | 0.71297 | 1782.15976 | −19.26178 | 2.95387 |
| | ethiofencarb | 200 | 41346.56830 | 0.67419 | 956.34086 | −17.69896 | 2.36322 |
| | XMC | 245 | 48304.67460 | 0.83167 | 7187.45738 | −22.81184 | 2.03264 |
| | metolcarb | 268 | 44415.60221 | 0.61559 | 549.74439 | −16.22158 | 2.52540 |
| | fenobucarb | 350 | 50302.85806 | 0.56719 | 379.15648 | −15.31158 | 2.79119 |
| | isoprocarb | 450 | 30154.52708 | 0.71158 | 1110.87846 | −18.10620 | 2.33776 |
| | butoxycarboxim | 458 | 62644.83638 | 0.72498 | 2617.19483 | −20.24395 | 1.96378 |

A BP neural network model was built with the above values.

Firstly, a relatively simple linear regression model was established by Logistic regression, and a multivariate linear regression formula was obtained. Because $R^2<0$, it was proved that the linear model was not suitable for studying the relationship between interaction information and $LD_{50}$ value. Then, nonlinear regression modeling was performed. Here, we had established seven commonly used nonlinear models, which were SVR regression, RandomForest regression, AdaBoost regression, xgboost.XGBRF regression, GradientBoosting regression, DecisionTree regression and back propagation regression. In Table 2, it is found that the average values of $R^2$ DecisionTree Regression and Back Propagation Regression are higher than 0.8, showing a relatively good fitting effect.

TABLE 2

Names and values of regression models

| Algorithm name | $R^2$ |
|---|---|
| Logistic Regression | −19.543 |
| SVR Regression | −55741.380 |
| RandomForest Regression | 0.307 |
| AdaBoost Regression | 0.146 |
| xgboost.XGBRF Regression | 0.697 |
| GradientBoosting Regression | 0.737 |
| DecisionTree Regression | 0.835 |
| Backpropagation Regression | 0.883 |

Therefore, the decision tree regression model and BP neural network model were optimized by adjusting parameters. It can be seen from Table 3 that $R^2$ of decision tree model and BP neural network model were 0.949 and 0.952, respectively, indicating that the fitting effect was greatly improved. Through the analysis of multiple regression models, it was determined that decision tree model and BP neural network model could have the best toxicity prediction effect.

TABLE 3

$R^2$ value optimized by adjusting parameters

| Algorithm name | $R^2$ |
|---|---|
| DecisionTree Regression | 0.949 |
| Backpropagation Regression | 0.952 |

Decision tree model was a simple algorithm with a tree structure composed of multiple nodes, which can be used to handle discrete data sets and continuous data sets. All the parameters in this study used the default values in python. Decision tree was a tree structure, in which each internal node represented an attribute test, each branch represented a test output, and each leaf node represented a category. Decision tree learning used top-down recursive method, and its basic idea was to build a tree with the fastest entropy decline as a measure of information entropy.

Figure 6:
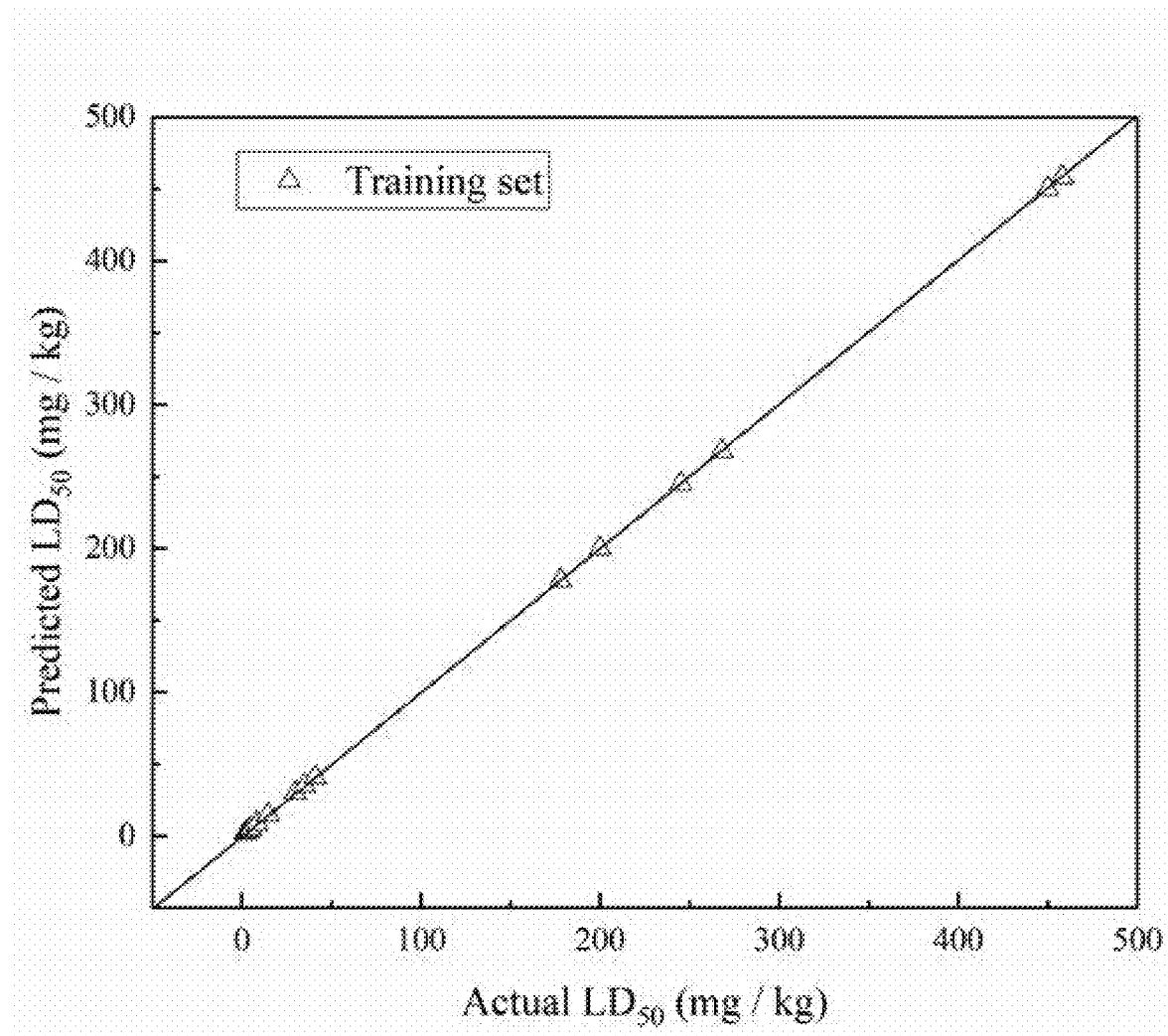
FIG. 6 shows the relationship between predicted $LD_{50}$ value and actual $LD_{50}$ value of BP model of training set.
Figure 7:
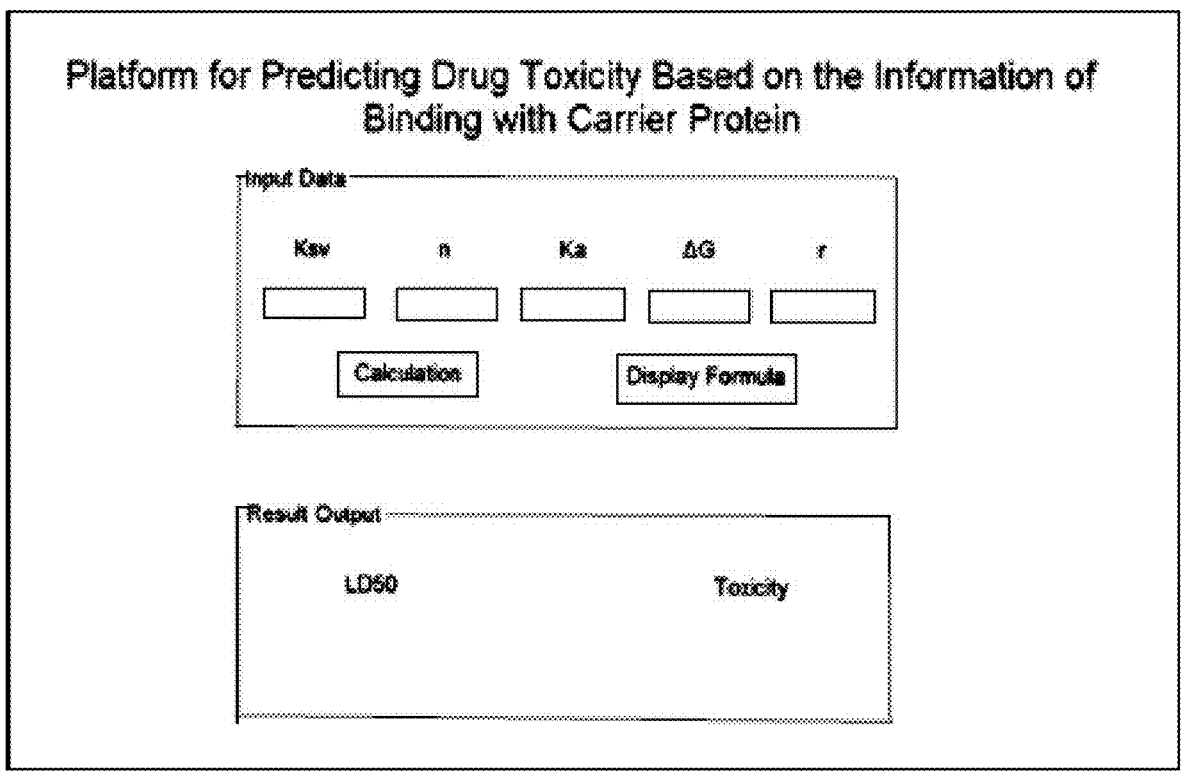
FIG. 7 shows a platform for predicting drug toxicity based on data on binding with carrier protein.

BP neural network was a multilayer feedforward network, which was trained by back propagation of the errors. Its algorithm was called BP algorithm, which used gradient search technology to form a network. Back propagation was used to adjust the weights and thresholds of the network to achieve the minimum error sum of squares. In this study, the default parameters in Matlab2019a were used. The fitting effect of the back propagation neural network model of the training set is shown in FIG. 6.

Figure 14:
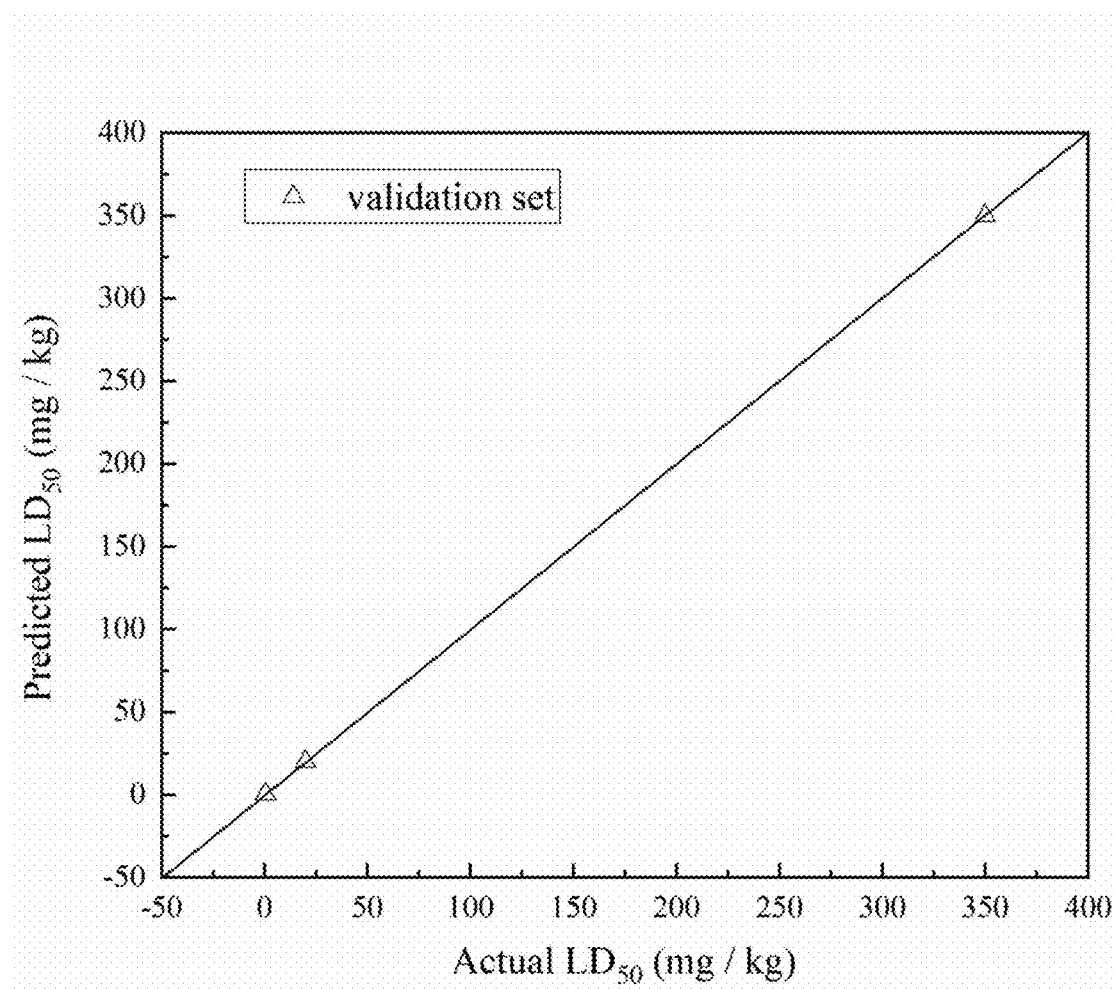
FIG. 14 shows the relationship between predicted $LD_{50}$ value and actual $LD_{50}$ value of BP model of prediction set.

In order to verify the prediction effect of the model, three other carbamate pesticides were selected for testing. Their spectral detection data and $LD_{50}$ values are shown in Table 4. The interaction between these three pesticides and HSA was studied by fluorescence spectroscopy. In Table 4, five modeling indexes including quenching constant, number of binding sites, binding constant, binding distance and free energy at 310 K were calculated. By inputting these data into the best two models, the predicted $LD_{50}$ value was obtained. It can be seen from Table 5 and Table 6 that the difference between the predicted $LD_{50}$ value of BP model and the true $LD_{50}$ value was the smallest, indicating that the prediction effect of BP neural network model was better than that of decision tree model. The fitting of the back propagation neural network model of the test set is shown in FIG. 14.

The $R^2$ value of decision tree model was similar to that of BP neural network model, but the prediction effect was far less than that of BP neural network model. This was because the decision tree model showed relatively low classification accuracy. Although this method can deal with high-dimensional and diverse features, it was also true in many chemoinformatics datasets. The biggest feature of BP model was that compared with traditional learning algorithms, it can randomly initialize the input weights and deviations and obtain the corresponding output weights for a single hidden layer neural network on the premise of ensuring the learning accuracy. According to the BP neural network model, it can be seen that there is a strong correlation between fluorescence spectrum information and toxicity, indicating that this method can be used to predict toxicity.

TABLE 4

Interaction information of three pesticides and HSA

| Substance name | T | $K_{sv}$ ($10^4$ M−1) | n | $K_a$ (M$^{-1}$) | $\Delta G^0$ (KJ · mol$^{-1}$) | r |
|---|---|---|---|---|---|---|
| Aldicarb | 296 | 6.498 ± 0.153 | 0.823 ± 0.002 | (8.438 ± 0.095) × $10^3$ | −22.263 | |
| | 303 | 6.999 ± 0.079 | 0.837 ± 0.002 | (1.069 ± 0.037) × $10^4$ | −23.341 | |
| | 310 | 7.230 ± 0.167 | 0.851 ± 0.002 | (1.294 ± 0.003) × $10^4$ | −24.419 | 2.623 |
| Aldicarb-sulfone | 296 | 2.797 ± 0.157 | 0.582 ± 0.008 | (2.589 ± 0.242) × $10^2$ | −13.649 | |
| | 303 | 3.379 ± 0.129 | 0.624 ± 0.003 | (4.548 ± 0.081) × $10^2$ | −15.471 | |
| | 310 | 3.984 ± 0.197 | 0.654 ± 0.010 | (8.295 ± 0.259) × $10^2$ | −17.294 | 2.376 |
| Fenobucarb | 296 | 3.803 ± 0.107 | 0.535 ± 0.006 | (1.894 ± 0.144) × $10^2$ | −12.911 | |
| | 303 | 4.110 ± 0.183 | 0.559 ± 0.004 | (2.724 ± 0.153) × $10^2$ | −14.111 | |
| | 310 | 5.030 ± 0.145 | 0.567 ± 0.008 | (3.792 ± 0.370) × $10^2$ | −15.312 | 2.791 |

TABLE 5

Prediction results of decision tree model

| | | | | Before optimization | | Optimized | |
|---|---|---|---|---|---|---|---|
| Substance name | Actual $LD_{50}$ (mg/kg) | predicted $LD_{50}$ (mg/kg) | Residual (SSE) | Predicted $LD_{50}$ (mg/kg) | Residual (SSE) | | |
| Aldicarb | 0.5 | 2.5 | 2 | 15.82 | 15.32 | | |
| Aldicarb-sulfone | 20 | 35 | 15 | 15.82 | 4.18 | | |
| Fenobucarb | 350 | 268 | 82 | 299.83 | 50.17 | | |

TABLE 6

Prediction results of BP neural network model

| | | | | Before optimization | | Optimized | |
|---|---|---|---|---|---|---|---|
| Substance name | Actual $LD_{50}$ (mg/kg) | Predicted $LD_{50}$ (mg/kg) | Residual (SSE) | Predicted $LD_{50}$ (mg/kg) | Residual (SSE) | | |
| Aldicarb | 0.5 | 1.7789 | 1.2789 | 0.56988 | 0.06988 | | |
| Aldicarb-sulfone | 20 | 21.4015 | 1.4015 | 20.0703 | 0.0703 | | |
| Fenobucarb | 350 | 350.9464 | 0.9464 | 350.0467 | 0.0467 | | |

SSE=predicted $LD_{50}$–actual $LD_{50}$.

Therefore, the BP neural network model had the best effect and the highest fitting degree in all data models. During the prediction, the above five values of the pesticide to be tested by fluorescence spectroscopy were input into the adjusted BP model, which could quickly fit the $LD_{50}$ value of the pesticide, and be used to quickly predict the toxicity of the new pesticide in the early stage, and provided data reference for whether the compound was valuable for further development. The $LD_{50}$ obtained was classified by the criteria for pesticide hazard classification standard from the World Health Organization to obtain the toxicity grade. The larger the value was, the lower the toxicity was, and the smaller the value was, the greater the toxicity was.

2. The influence of carbamate pesticides on the conformational changes of HSA was determined by synchronous fluorescence spectroscopy, specifically comprising:

The mixed solution to be tested was preheated at 283-232 K for 2-5 minutes, and the scanning speed was set at 300 nm/min; the excitation and emission spectra were scanned simultaneously in the range of 200-400 nm to obtain the synchronous fluorescence spectrum of HSA with carbamate pesticides. The interval between excitation wavelength and emission wavelength was set at 15 nm and 60 nm respectively. When $\Delta\lambda$=15 nm, the concentration of HSA was kept at $2\times10^{-6}$ M, and the concentration of the pesticide was $(0-42)\times10^{-6}$ m; when $\Delta\lambda$=60 nm, the concentration of HSA was kept at $5\times10^{-7}$ M, and the concentration of pesticide was $(0-105)\times10^{-7}$ M. Firstly, HSA was measured, and then the ratio of HSA to pesticide needed to be determined specifically, which was preliminarily determined according to the ratio of 1:1, 1:2 and 1:3.

Figure 8:
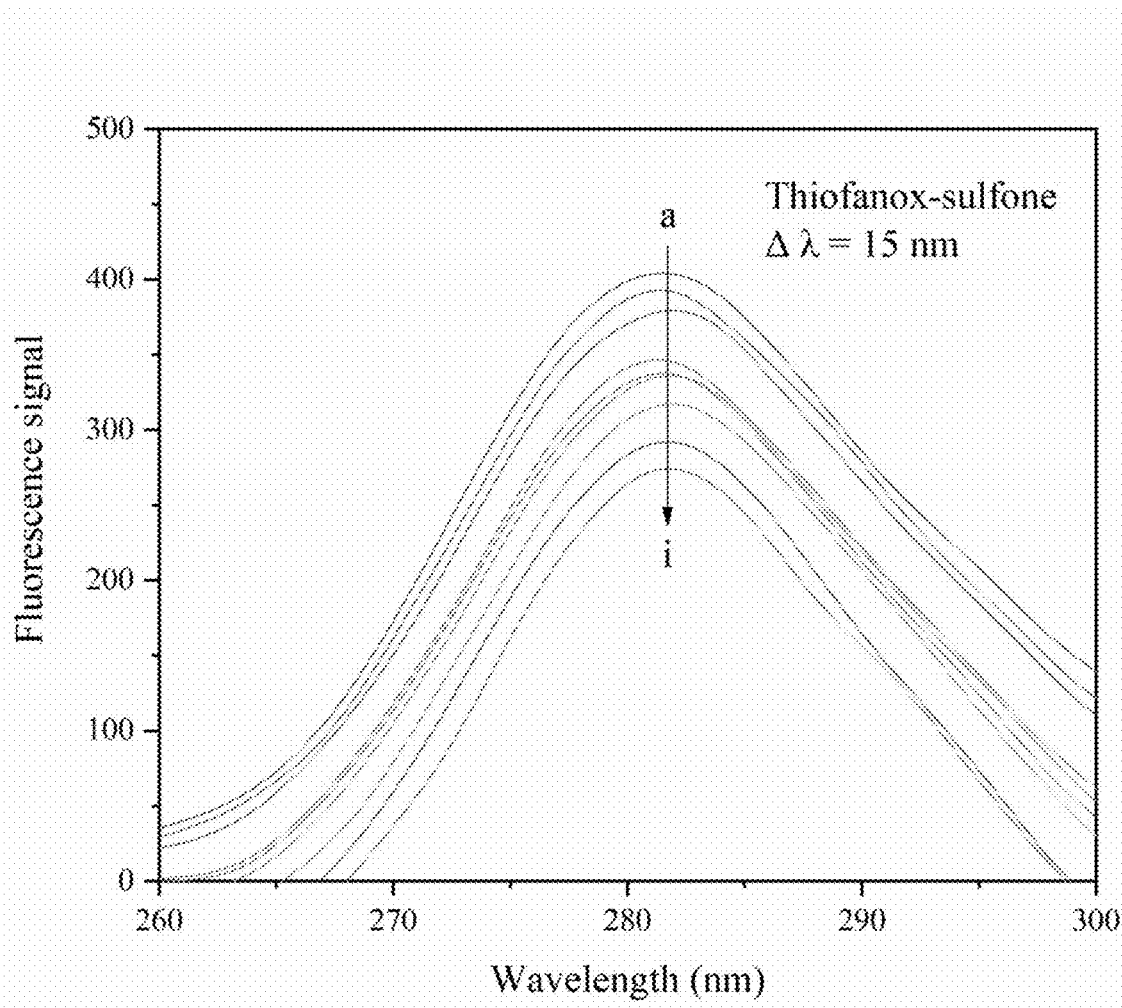
FIG. 8 shows the fluorescence signal of tyrosine residues measured by synchronous fluorescence spectrum with $\Delta\lambda=15$ nm, in which a-h represent HSA with different concentrations of thiofanox sulfone. When $\Delta\lambda=15$ nm, the HSA concentration is $2\times10^{-6}$, and the ratio of thiofanox sulfone to HSA is 0: 1, 3: 1, 6: 1, 9: 1, 12: 1, 15: 1, 18: 1 and 21: 1, respectively, pH=7.4, T=310 K, and i represents the serum albumin.
Figure 9:
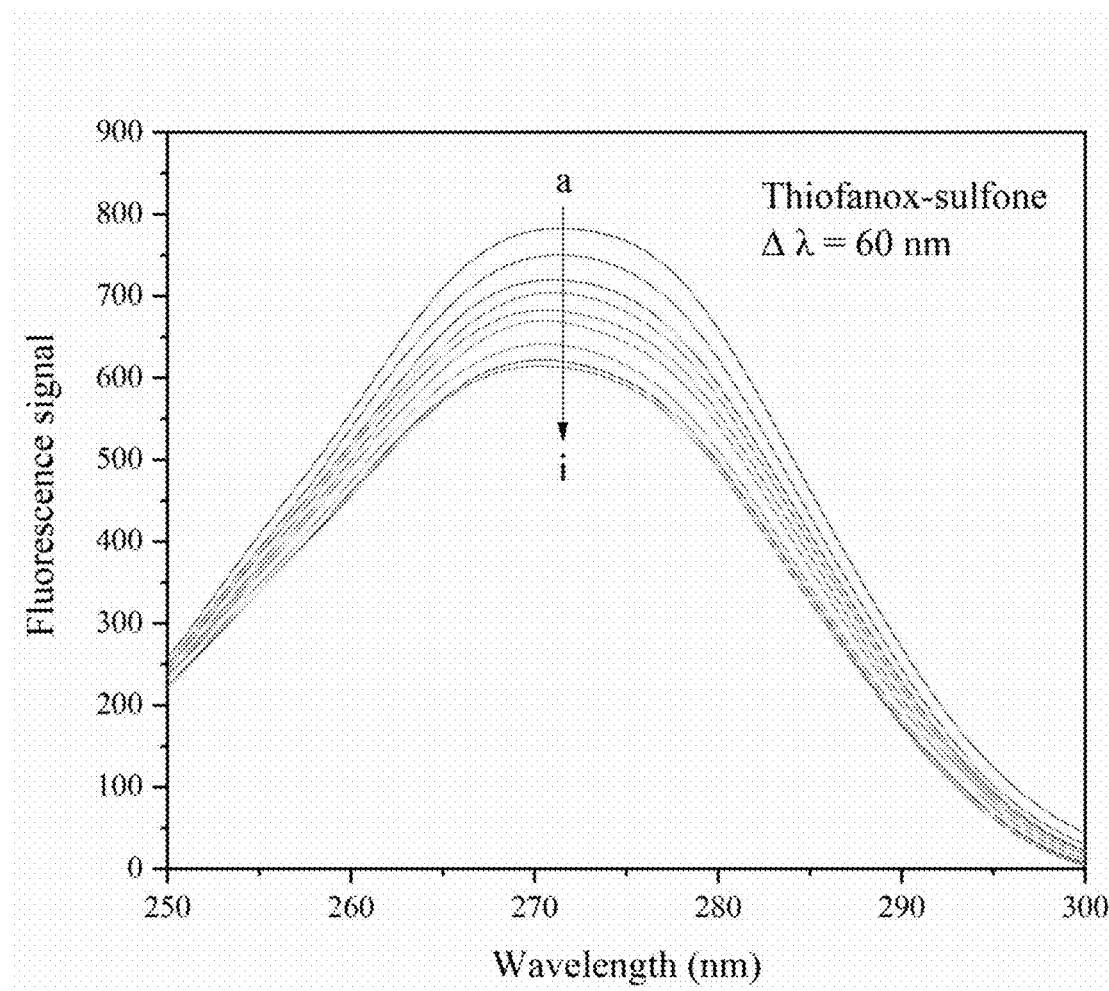
FIG. 9 shows the fluorescence signal of tryptophan residues measured by synchronous fluorescence spectrum with $\Delta\lambda=60$ nm, in which, a-h represent HSA with different concentrations of thiofanox sulfone. When $\Delta\lambda=60$ nm, the HSA concentration is $5\times10^{-7}$, and the ratio of thiofanox sulfone to HSA is 0: 1, 3: 1, 6: 1, 9: 1, 12: 1, 15: 1, 18: 1 and 21: 1, pH=7.4, T=310 K, and i represents the serum albumin.

Conclusion: The synchronous fluorescence spectrum with $\Delta\lambda$=15 nm can only show the fluorescence of tyrosine residues, as shown in FIG. 8, while the synchronous fluorescence spectrum with $\Delta\lambda$=60 nm can only show the fluorescence of tryptophan residues, as shown in FIG. 9. The change of conformation of protein can be judged by the change of emission wavelength, because the maximum emission wavelength of amino acid residues is related to the hydrophobicity of its environment. The experimental results show that with the increase of drug concentration, the maximum fluorescence emission peak of protein decreases under the spectra of $\Delta\lambda$=15 nm and $\Delta\lambda$=60 nm . This indicates that the microenvironment around tyrosine and tryptophan changes slightly.

Figure 10:
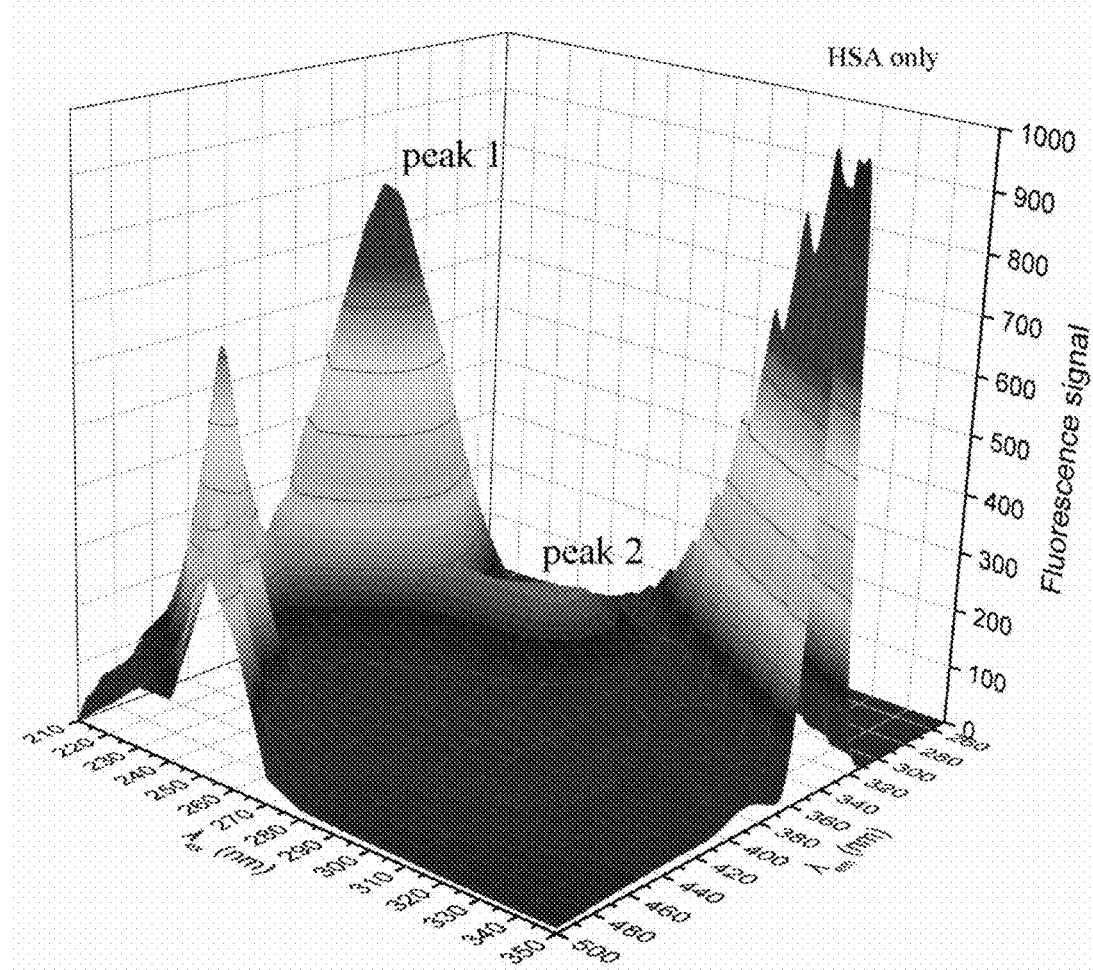
FIG. 10 is a conformational diagram of HSA measured by three-dimensional fluorescence spectrum.
Figure 11:
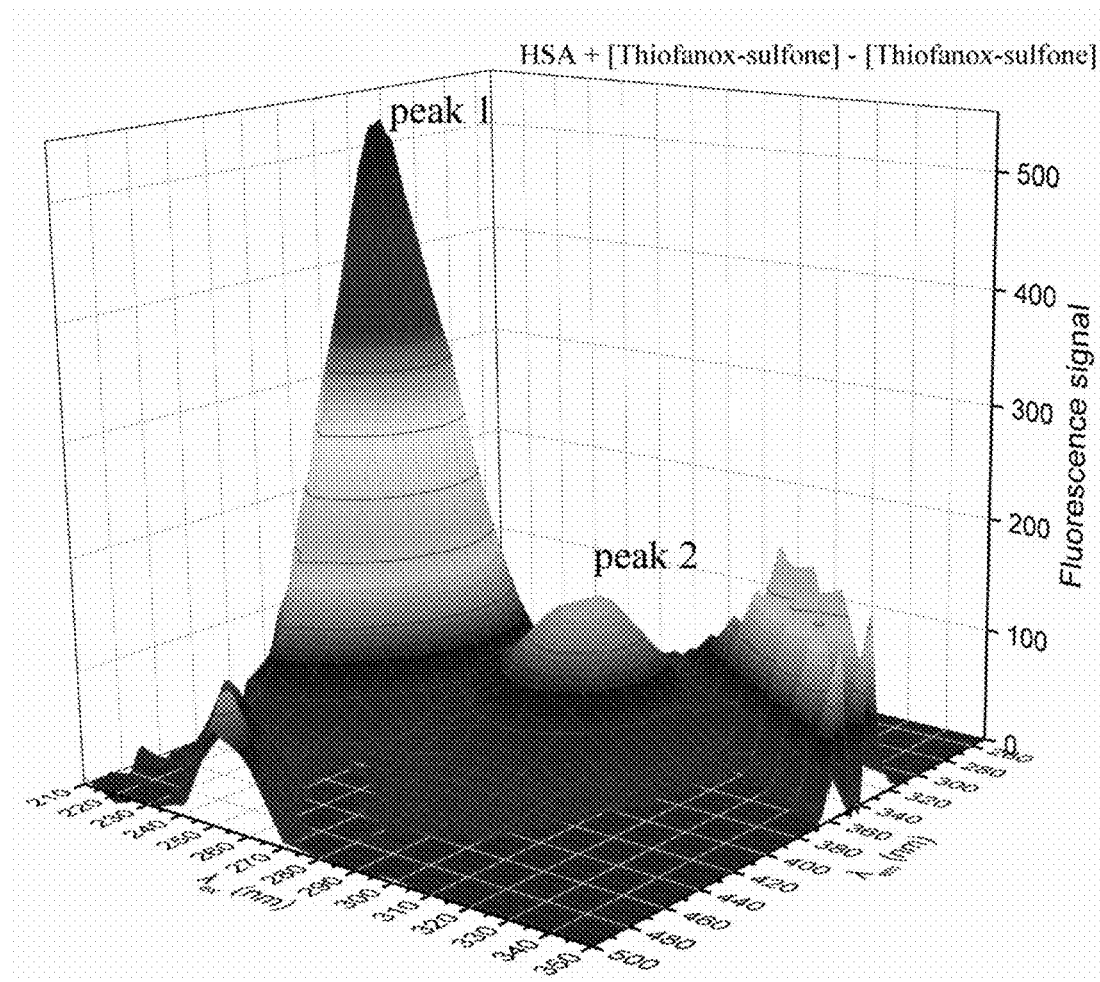
FIG. 11 shows the conformational change of HSA caused by thiofanox sulfone measured by three-dimensional fluorescence spectroscopy.

3. The influence of carbamate pesticides on the conformational changes of HSA was determined by three-dimensional fluorescence spectroscopy. Specifically the procedure was conducted as follows:

The mixed solution to be tested was preheated at 283-232 K for 2-5 minutes, and the scanning speed was set at 300 nm /min. The three-dimensional fluorescence spectra of $8\times10^{-8}$ M HAS and $8\times10^{-8}$ M HSA for mixed with $8\times10^{-7}$M pesticides were analyzed respectively. As shown in FIG. 10 and FIG. 11, it was recorded that the emission wavelength was 250-500 nm, the initial excitation wavelength was set at 210 nm , the excitation interval was 10 nm , and the slit width for both excitation and emission was 15 nm. Firstly, HSA was measured, and then the ratio of HSA to pesticides needed to be determined specifically, which was preliminarily determined according to the ratio of 1:1, 1:2 and 1:3.

Conclusion: According to the measured results, peak 1 mainly shows the fluorescence spectral behavior of polypeptide skeleton structure, while peak 2 mainly shows the spectral characteristics of tryptophan and tyrosine residues. After adding the pesticides, the fluorescence signal of peak 1 decreases significantly, indicating that the microenvironment around the polypeptide skeleton structure has changed. The signal of peak 2 also decreases but was not significant, indicating that the microenvironment around tryptophan and tyrosine has changed slightly.

4. The changes of secondary structure of white protein in human serum caused by carbamate pesticides were determined by circular dichroism spectrum, specifically comprising:

the mixed solution to be tested was preheated at 283-232 K for 2-5 minutes, and the CD spectrum of HSA was recorded in the wavelength range of 200-500 nm . The concentration of HSA was kept at $2 \times 10^{-6}$ M, and the pesticide was $(0-20) \times 10^{-6}$ m. Firstly, HSA was measured, and then the ratio of HSA to pesticides needed to be determined specifically, which was preliminarily determined according to the ratio of 1:1, 1:2 and 1:3.

Figure 12:
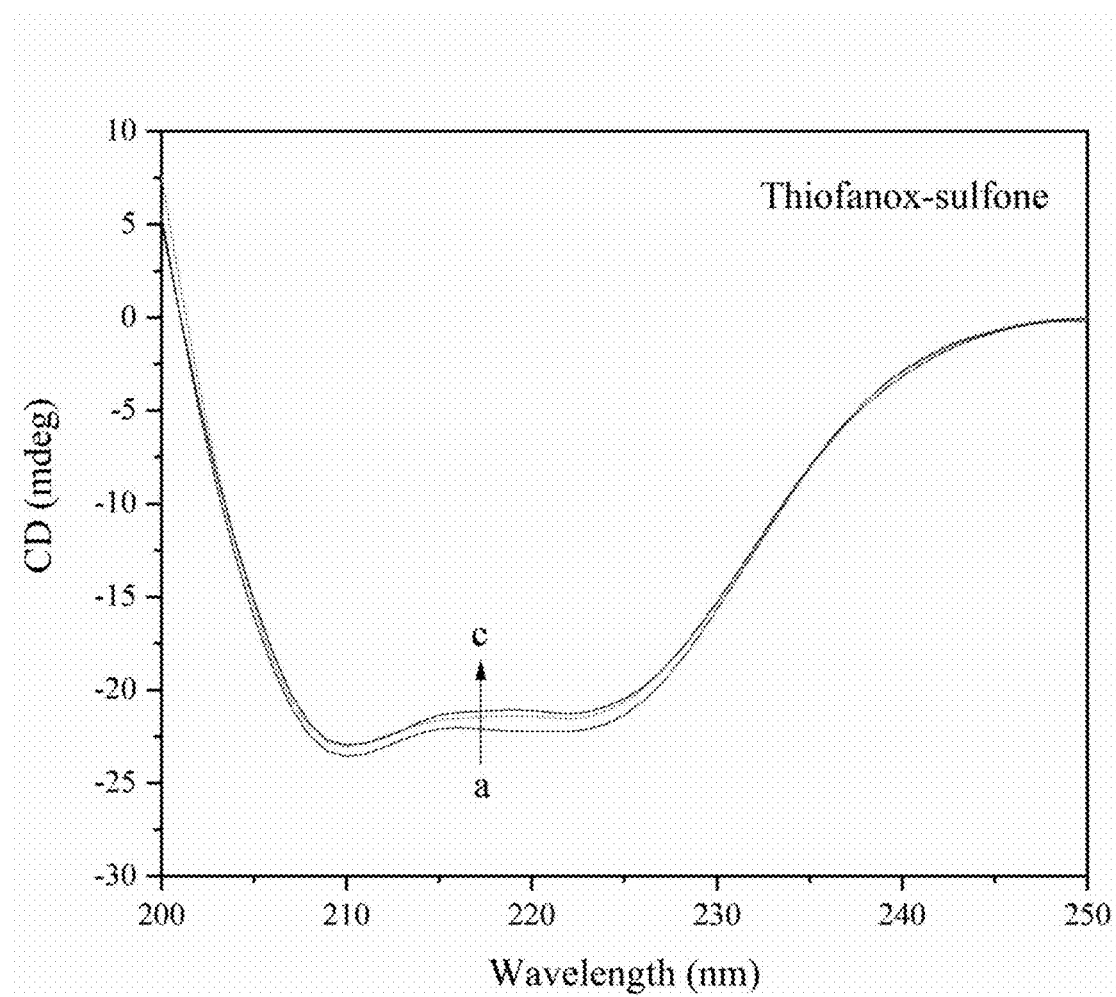
FIG. 12 shows the change of secondary structure of HSA caused by thiofanox sulfone measured by circular dichroism spectrum, in which a represents $2\times10^{-6}$ M HSA only; (b-c) represent HSA ($2\times10^{-6}$ M) with thiofanox sulfone, the ratio of thiofanox sulfone to HSA is 5: 1, 10: 1, pH=7.4, and T=296 K.

Conclusion: CD spectra of free HSA and HSA pesticide system are tested. HSA shows negative Cotton effect at 208 nm and 222 nm , suggesting a typical α-helix structure. After adding pesticides, the negative effects of HSA on Cotton at 208 nm and 222 nm are reduced. The circular dichroism shape of HSA has not changed, indicating that the secondary structure of protein in the system is still dominated by a-helix structure, as shown in FIG. 12. In the following table, the changes of α-helix content of different pesticides are calculated.

TABLE 7

Changes of α-helix content of different pesticides

| Substance name | α-helix contents | | |
|---|---|---|---|
| | HSA only | 5:1 (Pesticide:HSA) | 10:1 (Pesticide:HSA) |
| Thiofanox-sulfone | 52.445% | 51.076% | 50.482% |
| Oxamyl | 52.768% | 50.883% | 49.354% |
| Thiofanox-sulfoxide | 51.829% | 50.523% | 48.338% |
| Carbofuran | 53.567% | 51.483% | 48.304% |
| Thiofanox | 51.371% | 48.904% | 48.180% |
| Methomyl | 51.353% | 50.756% | 49.970% |
| Aminocarb | 52.156% | 49.862% | 49.082% |
| Promecarb | 52.255% | 48.610% | 48.538% |
| Propoxur | 50.393% | 50.121% | 49.341% |
| Dimethacarb | 54.683% | 52.233% | 48.283% |
| Ethiofencarb | 50.640% | 49.087% | 48.340% |
| XMC | 56.422% | 55.392% | 54.416% |
| Metolcarb | 55.607% | 53.549% | 53.215% |
| Isoprocarb | 53.205% | 50.878% | 49.242% |
| Butoxycarboxim | 56.793% | 53.753% | 52.790% |

According to the following equation, the result of CD spectrum was usually expressed as the mean residue ellipticity (MRE), and the unit was deg·cm²·dmol⁻¹.

$$MRE = ObservedCD(mdeg)/(10Cpnl) \quad (9);$$

in which Cp is the molar concentration of protein, n is the number (585) of amino acid residues, and l is the path length (1 mm). The α helicity of free and bound HSA is calculated from MRE values using the following formula:

$$\alpha\text{-Helix}(\%) = [(-MRE_{208} - 4000) \times 100]/(33000 - 4000) \quad (10)$$

in which the MRE208 is the MRE value observed at 208 nm , 4000 is the MRE value of random coil conformation at 208 nm , and 3000 is the MRE value of pure α helix at 208 nm .

Table 7 shows the changes of α-helix content before and after pesticide addition. With the increase of compound content, the α-helix content of HSA decreases slightly, indicating that the protein conformation changes after adding compound.

5. The influence of carbamate pesticides on HSA determined by using UV-vis absorption spectrum, specifically comprising:

the mixed solution to be tested was preheated at 283-232 K for 2-5 minutes, the UV-vis spectrum of HSA added with various drugs in the range of 190-500 nm was recorded, the wavelength interval was set at 0.5 nm and the slit width was set at 2 nm . HSA in the system was fixed at a concentration of $5 \times 10^{-6}$M and titrated with $(0-175) \times 10^{-6}$ M pesticides.

Figure 13:
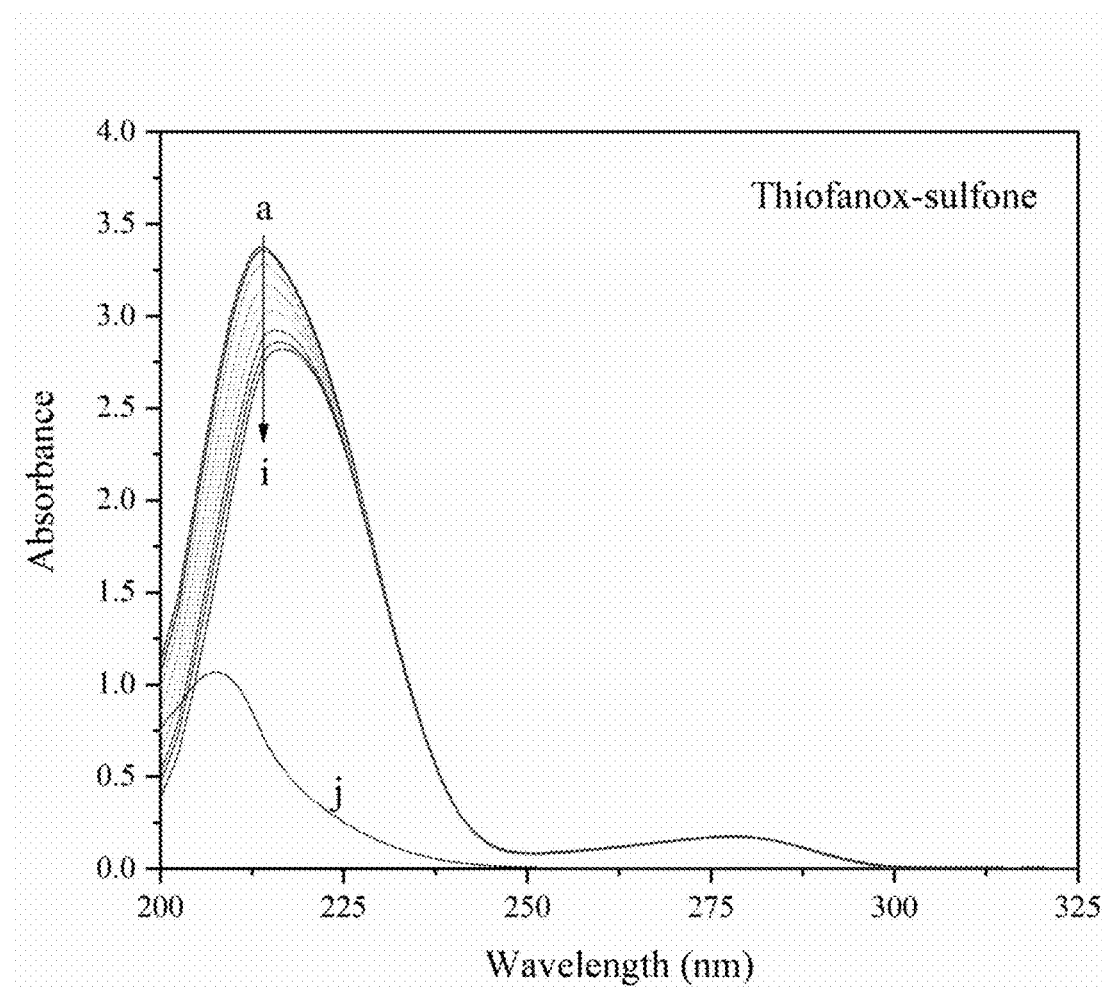
FIG. 13 is a spectrogram showing effects of thiofanox sulfone on HSA measured by UV-Vis absorption spectrum, in which (a) represents $5\times10^{-6}$ M HSA only; (b-i) represents HSA ($2\times10^{-6}$ M) with pesticide, the ratio of pesticide to HSA is 1:1, 5:1, 10: 1, 15:1, 20:1, 25:1, 30:1; (j) represents $5\times10^{-6}$ M pesticide only, pH=7.4, and T=310 K.

Conclusion: The UV-vis spectrum shows that HSA has two characteristic absorption peaks at about 212 nm and 278 nm , respectively. The strong absorption peak around 212 nm reflects HSA's absorption of peptide skeleton structure, while the weak absorption peak around 278 nm is produced by aromatic amino acids (Trp, Tyr and Phe). The results show that after adding pesticides, it shows the same trend. As shown in FIG. 13, the UV-vis absorption of HSA at 212 nm decreases, while the weak absorption near 278 nm does not change significantly. The results indicates that the polarity of microenvironment near peptide skeleton increases, while microenvironment near aromatic amino acids changes slightly.

In addition, UV-vis spectra can be used to determine the quenching mechanism between dynamic quenching and static quenching. Dynamic quenching only affects the excited state of fluorophore, but does not affect the absorption spectrum of fluorophore. However, due to the formation of complexes, the absorption of fluorophores is constantly changing. The absorption spectra of different concentrations of pesticides on HSA can confirm that the reaction mechanism between these pesticides and HSA is static quenching.

Aromatic amino acid (tryptophan residues, tyrosine residues and phenylalanine residues) is the only amino acid residue in HSA that can emit fluorescence. The intrinsic fluorescence of HSA is mainly caused by tryptophan at position 214. At 310 K, the fluorescence emission spectra and ultraviolet spectra with/without the thiofanox sulfone. It can be seen that the fluorescence signal of HSA decreases with the titration of pesticides, accompanied by occurrence of a blue shift phenomenon, indicating that the fluorescence of HSA is quenched by thiofanox sulfone, and HSA is also quenched by other 14 carbamate pesticides after detection.

In the use of the protein in predicting drug properties, the interaction information between the drug and HSA through ultraviolet-visible spectrum, fluorescence, synchronous fluorescence, three-dimensional fluorescence, circular dichroism (CD) spectrum and molecular docking technology are systematically studied. In order to predict toxicity more easily with the least equipment and time, eight regression models and eight classification models for five indexes (quenching constant, number of binding sites, binding constant, free energy and binding distance) are obtained by fluorescence spectrum and toxicity. By comparing the predicted $LD_{50}$ values obtained from this model with the actual $LD_{50}$ values of other three carbamate pesticides, the best two new models are further verified. In this study, a new method for predicting the toxicity of carbamate pesticides (CPBITR) is constructed, and more importantly, it provides a new and unique perspective (combined with carrier protein) for predicting drug toxicity for the first time. This research is of important practical significance to the development of drug research and development industry.

What is claimed is:

1. A method for predicting the toxicity of a drug, wherein the method comprising:
    (1) preparing a buffer solution: preparing a 0.02 M phosphate buffer solution with pH value of 7.4;

(2) preparing a protein diluent: dissolving and diluting a protein solution with the buffer solution prepared in step (1) to obtain a protein diluent;

(3) preparing a detection solution: mixing the protein diluent prepared in step (2) with a drug to be tested in a molar ratio of protein to drug of 1: (1-300) to obtain a mixed solution to be tested, and predicting the properties of the drug by using fluorescence emission spectrum, and wherein the protein comprises human serum albumin (HSA), bovine serum albumin, hemoglobin, globulin, myogenic, collagen, zymoprotein, bee protein and fish protein, the method for predicting the drug toxicity further comprises a step of preheating the mixed solution to be tested at 232-283 K for 3 minutes, and measuring fluorescence emission spectrum of the protein mixed with the drugs at 300-500 nm, an excitation wavelength is 280 nm, and a slit width for both excitation and emission are 15 nm; concentration of the protein is $5\times10^{-7}$ M, and the concentration of the drug is $(0-105)\times10^{-7}$ M;

correcting an internal filtering effect of fluorescence signal according to the following formula:

$$F_{cor}=F_{obs}\exp[(A_{ex}+A_{em})/2] \quad (1);$$

in this formula, $F_{cor}$ and $F_{obs}$ represent corrected fluorescence signal and observed fluorescence signal, respectively, and $A_{ex}$ and $A_{em}$ represent absorbance of the mixed solution to be tested at excitation wavelength and emission wavelengths, respectively, wherein the drug is a pesticide selected from the group consisting of aldicarb, oxamyl, thiofanox sulfone, carbofuran, thiofanox, methomyl, aldicarb sulfone, aminocarb, promecarb, propoxur, dimethacarb, ethiofencarb, XMC (3,5-xylyl methylcarbamate), metolcarb, fenobucarb, isoprocarb and butoxycarboxim, wherein the method for predicting the drug toxicity further comprises a step of obtaining five values comprising a quenching constant, a binding constant, a number of binding sites, a binding distance and a free energy of the drug by fluorescence emission spectra, and then constructing a model using a backpropagation neural network, obtaining an $LD_{50}$ value of the drug by inputting into the model the said five values detected by fluorescence spectrum of the drug, and obtaining a toxicity grade according to the criteria for pesticide hazard classification from the World Health Organization, thus completing a toxicity prediction.

2. The method according to claim 1, wherein the protein is HSA.

3. The method according to claim 1 in predicting drug properties, wherein molar ratio of the protein diluent to the drug to be tested is 1:(1-100).

* * * * *